(12) United States Patent
Kim et al.

(10) Patent No.: US 9,921,280 B2
(45) Date of Patent: Mar. 20, 2018

(54) BIOMAGNETIC RESONANCE DEVICE AND MEASURING METHOD THEREFOR

(71) Applicant: Korea Research Institute of Standards and Science, Daejeon (KR)

(72) Inventors: Kiwoong Kim, Daejeon (KR); Yong-ho Lee, Daejeon (KR); Seong-Joo Lee, Daejeon (KR); Kwon-Kyu Yu, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 884 days.

(21) Appl. No.: 14/446,764

(22) Filed: Jul. 30, 2014

(65) Prior Publication Data

US 2014/0343397 A1 Nov. 20, 2014

Related U.S. Application Data

(63) Continuation of application No. PCT/KR2012/010901, filed on Dec. 14, 2012.

(30) Foreign Application Priority Data

Jan. 31, 2012 (KR) .................. 10-2012-0009363

(51) Int. Cl.
*A61B 5/055* (2006.01)
*G01R 33/385* (2006.01)
(Continued)

(52) U.S. Cl.
CPC .............. *G01R 33/385* (2013.01); *A61B 5/05* (2013.01); *A61B 5/055* (2013.01); *G01R 33/26* (2013.01);
(Continued)

(58) Field of Classification Search
None
See application file for complete search history.

(56) References Cited

U.S. PATENT DOCUMENTS 5,274,331 A * 12/1993 Macovski ............ G01R 33/445
324/307
5,291,138 A * 3/1994 Macovski ............ G01R 33/445
324/307

(Continued)

FOREIGN PATENT DOCUMENTS

JP  2003-515405 A   5/2003
JP  2004-160223 A   6/2004
(Continued)

OTHER PUBLICATIONS

International Search Report for Application No. PCT/KR 2012/010901 dated Mar. 22, 2013.

*Primary Examiner* — Jonathan Cwern
(74) *Attorney, Agent, or Firm* — Jenkins, Wilson, Taylor & Hunt, P.A.

(57) ABSTRACT

Provided are an ultra-low-field nuclear magnetic resonance device and an ultra-low-field nuclear magnetic resonance measuring method. The method includes applying a first measurement bias magnetic field corresponding to an excitation frequency of a coherent biomagnetic field generated in association with the electrophysiological activity of human body organs, applying a second measurement bias magnetic field having the same direction as the first measurement bias magnetic field and having a different magnitude than the first measurement bias magnetic field, and measuring a magnetic resonance signal generated in the human body by using magnetic field measuring means.

21 Claims, 16 Drawing Sheets

(51) Int. Cl.
  *G01R 33/32* (2006.01)
  *G01R 33/26* (2006.01)
  *G01R 33/48* (2006.01)
  *A61B 5/05* (2006.01)
  *G01R 33/44* (2006.01)

(52) U.S. Cl.
  CPC ......... *G01R 33/326* (2013.01); *G01R 33/445* (2013.01); *G01R 33/48* (2013.01); *G01R 33/4806* (2013.01)

(56) References Cited

U.S. PATENT DOCUMENTS

| | | |
|---|---|---|
| 8,044,663 B2 | 10/2011 | Kim et al. |
| 8,350,568 B2 | 1/2013 | Hwang et al. |
| 8,427,146 B2 | 4/2013 | Nagasaka |
| 2002/0069242 A1 | 6/2002 | Berns |
| 2003/0011368 A1* | 1/2003 | Abe ................... G01R 33/563 324/309 |
| 2007/0018643 A1* | 1/2007 | Clarke ............... G01R 33/0356 324/301 |
| 2007/0252595 A1* | 11/2007 | Volegov ................ A61B 5/055 324/307 |
| 2008/0161678 A1 | 7/2008 | Miyazaki et al. |
| 2008/0187196 A1* | 8/2008 | Hu ..................... G01R 33/5611 382/128 |
| 2009/0128272 A1* | 5/2009 | Hills ................... G01R 33/383 335/306 |
| 2011/0190619 A1* | 8/2011 | Good ................. G01R 33/0354 600/410 |
| 2012/0001631 A1* | 1/2012 | Espy ..................... G01N 24/08 324/309 |

FOREIGN PATENT DOCUMENTS

| | | |
|---|---|---|
| KR | 10-1012763 B1 | 2/2011 |
| KR | 10-1050153 61 | 7/2011 |

* cited by examiner

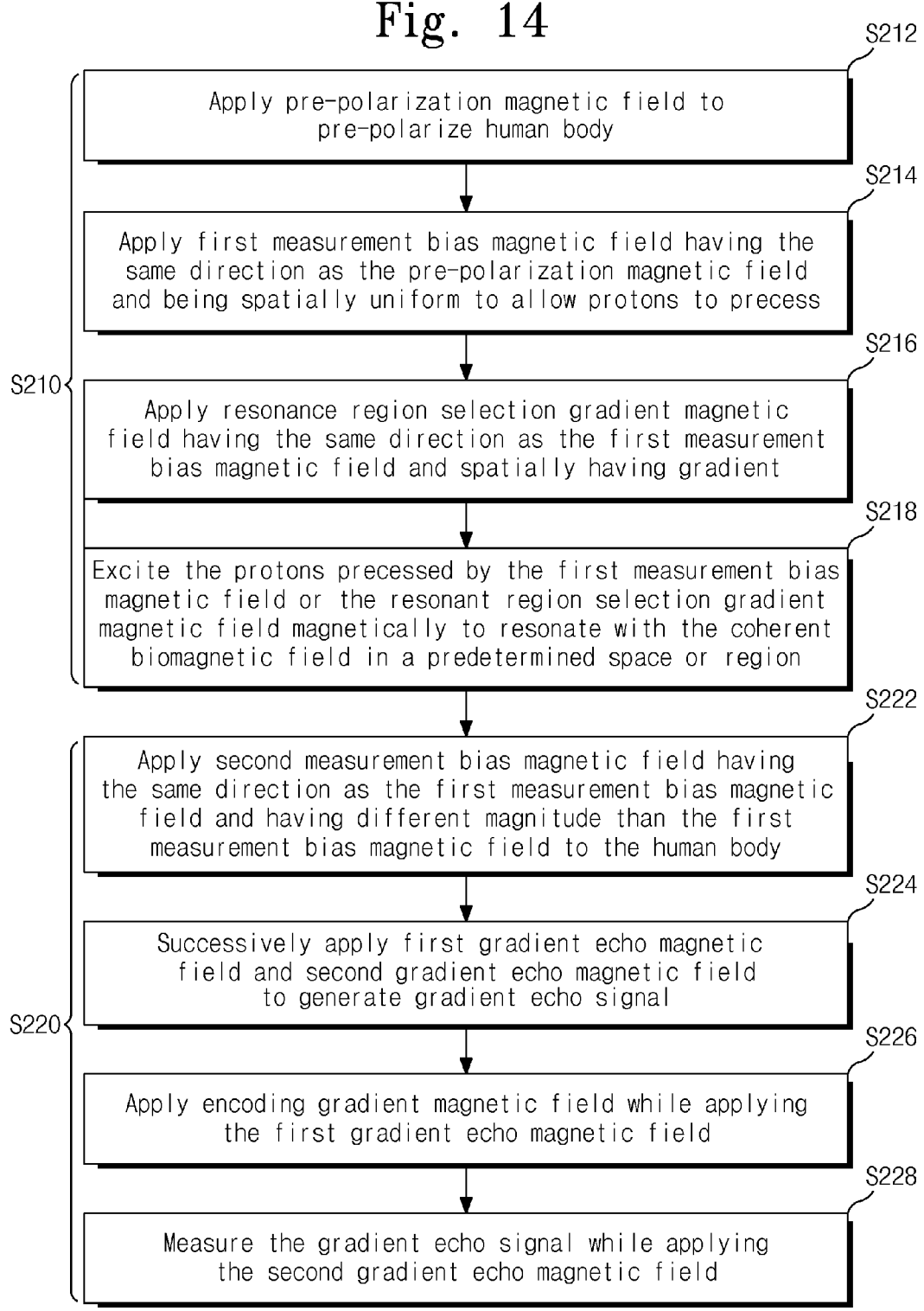

BIOMAGNETIC RESONANCE DEVICE AND MEASURING METHOD THEREFOR

CROSS-REFERENCE TO RELATED APPLICATION

This application is a continuation of and claims priority to PCT/KR2012/010901 filed on Dec. 14, 2012, which claims priority to Korea Patent Application No. 10-2012-0009363 filed on Jan. 31, 2012, the entirety of which is hereby incorporated by reference.

BACKGROUND

1. Field of the Invention

The present invention described herein generally relates to ultra-low-field nuclear magnetic resonance methods and, more particular, to ultra-low-field nuclear magnetic resonance methods in which an external excitation magnetic field is replaced with a bio-oscillating magnetic field.

2. Description of the Related Art

Many heart diseases are caused by reentry excitation or ectopic excitation of myocardium. Such a conduction abnormality develops atrial arrhythmia, tarchycardia, and heart failure that cause a stroke. Moreover, myocardial conduction abnormality is the mechanism of ventricular fibrillation that causes sudden cardiac death resulting from cardiac arrest. Conventionally, in order to detect myocardial conduction abnormality, a catheter electrode is inserted through aorta and vena cava of the thigh to measure endocardial potentials one by one while changing positions. Alternatively, a multichannel electrode patch is attached to the epicardium during thoracotomy surgery to measure the endocardial potentials. A non-invasive method includes electrocardiogram (ECG) in which a plurality of electrodes are attached to thorax and limbs to measure a potential and magnetocardiogram (MCG) in which myocardial electrical activity is measured using an ultra-sensitive magnetic sensor such as a superconducting quantum interference device (SQUID) or an atomic magnetometer.

SUMMARY

A subject matter of the present invention is to measure a nuclear magnetic resonance signal using a biomagnetic field and to image the measured nuclear magnetic resonance signal.

An ultra-low-field nuclear magnetic resonance measuring method according to an embodiment of the present invention may include applying a first measurement bias magnetic field with a Larmor frequency corresponding to an oscillation frequency of a periodical coherent biomagnetic field generated in association with the electrophysiological activity of human body organs; applying a second measurement bias magnetic field having the same direction as the first measurement bias magnetic field and having a different magnitude than the first measurement bias magnetic field; and separating a frequency of a magnetic resonance signal generated in the human body from the oscillation frequency of the biomagnetic field by applying the second measurement bias magnetic field and measuring the magnetic resonance signal using magnetic field measuring means.

In an embodiment of the present invention, the coherent biomagnetic field may have a component on a plane perpendicular to the first measurement bias magnetic field.

In an embodiment of the present invention, the ultra-low-field nuclear magnetic resonance measuring method may further include applying a pre-polarization magnetic field to pre-polarize the human body using pre-polarizing means; and deactivating the pre-polarization magnetic field before measuring the magnetic resonance signal.

In an embodiment of the present invention, a direction of the pre-polarization magnetic field may match that of the first measurement magnetic field.

In an embodiment of the present invention, the ultra-low-field nuclear magnetic resonance measuring method may further include scanning the magnitude of the first measurement bias magnetic field such that a proton magnetic resonance frequency of the first measurement bias magnetic field matches the oscillation frequency of the coherent biomagnetic field.

In an embodiment of the present invention, the magnetic field measuring means may be a superconducting quantum interference device or an optically pumped atomic magnetometer.

In an embodiment of the present invention, the ultra-low-field nuclear magnetic resonance measuring method may further include providing a gradient magnetic field to the human body.

In an embodiment of the present invention, the gradient magnetic field may include at least one of a resonance region selection gradient magnetic field, a gradient echo magnetic field, and an image encoding gradient magnetic field.

In an embodiment of the present invention, the resonance region selection gradient magnetic field may include at least one of a first resonance region selection gradient magnetic field, a second resonance region selection gradient magnetic field, and a third resonance region selection gradient magnetic field. The first resonance region selection gradient magnetic field, the second resonance region selection gradient magnetic field, and the third resonance region selection gradient magnetic field may provide gradient magnetic fields with respect to different directions. The resonance region selection gradient magnetic field may be applied before the second measurement bias magnetic field is applied.

In an embodiment of the present invention, the magnitude of the resonance region selection magnetic field may be scanned such that the sum of the magnitudes of the resonance region selection magnetic field and the magnitude of the first measurement magnetic field corresponds to an oscillation frequency of the coherent biomagnetic field.

In an embodiment of the present invention, the gradient echo magnetic field may applied after a second measurement bias magnetic field is applied. The gradient echo magnetic field may include a first gradient echo magnetic field and a second gradient echo magnetic field that are successively generated. The first gradient echo magnetic field and the second gradient echo magnetic field may be opposite in direction.

In an embodiment of the present invention, the encoding gradient magnetic field may be applied after a second measurement bias magnetic field is applied. The encoding gradient magnetic field may include at least one of a first encoding gradient magnetic field and a second encoding gradient magnetic field. The encoding gradient magnetic field may perform at least one of frequency encoding and phase encoding.

A nuclear magnetic resonance measuring method according to an embodiment of the present invention may include selecting a resonant region such that a coherent biomagnetic field having an oscillation frequency generated in association with electrophysiological activity of human organs magnetically resonates with protons precessing by a first measurement bias magnetic field; and spatially imaging a resonant region selected under a second measurement bias magnetic field having the same direction as the first measurement bias magnetic field and having different magnitude than the first measurement bias magnetic field.

In an embodiment of the present invention, selecting the resonant region may include at least one of applying a pre-polarization magnetic field to pre-polarize a human body; applying a first measurement bias magnetic field having the same direction as the pre-polarization magnetic field and being spatially uniform to allow protons to precess; applying a resonance region selection gradient magnetic field having the same direction as the first measurement bias magnetic field and spatially having a gradient; and exciting the protons precessed by the first measurement bias magnetic field or the resonance region selection gradient magnetic field magnetically to resonate with the coherent biomagnetic field in a predetermined space or regionresonance region selection.

In an embodiment of the present invention, spatially imaging a resonant region may include at least one of applying a second measurement bias magnetic field having the same direction as the first measurement bias magnetic field and having different magnitude than the first measurement bias magnetic field to the human body; successively applying a first gradient echo magnetic field and a second gradient echo magnetic field to generate a gradient echo signal; applying an encoding gradient magnetic field while applying the first gradient echo magnetic field; and measuring the gradient echo signal while applying the second gradient echo magnetic field.

In an embodiment of the present invention, the encoding gradient magnetic field may include at least one of a phase encoding gradient magnetic field and a frequency encoding gradient magnetic field.

An ultra-low-field nuclear magnetic resonance measuring device according to an embodiment of the present invention may include magnetically shielding means; magnetic field measuring means disposed adjacent to a measurement target disposed inside the magnetically shielding means; and measurement bias magnetic field generating means for applying a first measurement bias magnetic field corresponding to a proton magnetic resonance frequency matching an oscillation frequency of a coherent biomagnetic field generated in association with electrophysiological activity of human organs and successively changing the magnitude of the first measurement bias magnetic field to apply a second measurement bias magnetic field. The magnetic field measuring means measures a magnetic resonance signal generated from the measurement target.

In an embodiment of the present invention, the ultra-low-field nuclear magnetic resonance measuring device may further include pre-polarizing means for pre-polarizing the measurement target.]

In an embodiment of the present invention, the ultra-low-field nuclear magnetic resonance measuring device may further include gradient magnetic field generating means for providing a gradient magnetic field to the measurement target.

In an embodiment of the present invention, the gradient magnetic field generating means may include at least one of resonance region selection gradient echo magnetic field generating means for selecting a resonant region; gradient echo magnetic field generating means for generating a gradient echo signal; and encoding gradient magnetic field generating means for generating an encoding gradient magnetic field.

In an embodiment of the present invention, the first measurement bias magnetic field may be scanned.

According to another aspect of the present invention, an embodiment of the present invention may provide a brain functional connectivity measuring method for measuring and spatially imaging a magnetic resonance signal generated from protons resonating by a coherent biomagnetic field of a specific frequency in a human brain by using an ultra-low-field nuclear magnetic resonance device to detect brain function connectivity.

According to another aspect of the present invention, an embodiment of the present invention may provide a brain functional connectivity measuring method for measuring and spatially imaging a magnetic resonance signal generated from protons resonating by a coherent biomagnetic field of a specific frequency in a human brain by using an ultra-low-field nuclear magnetic resonance device to detect brain functional connectivity. The brain function connectivity measuring method may include applying a first measurement bias magnetic field with a Larmor frequency corresponding to an oscillation frequency of a brainwave magnetic field generated in association with the brain function connectivity; applying a second measurement bias magnetic field having the same direction as the first measurement bias magnetic field and having a different magnitude than the first measurement bias magnetic field; and separating a frequency of a magnetic resonance signal generated in the brain from the oscillation frequency of the brainwave magnetic field by applying the second measurement bias magnetic field and measuring the magnetic resonance signal using magnetic field measuring means.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present invention.

FIG. 14 is a flowchart summarizing a nuclear magnetic resonance measuring method according to another embodiment of the present invention.

DETAILED DESCRIPTION

Figure 1:
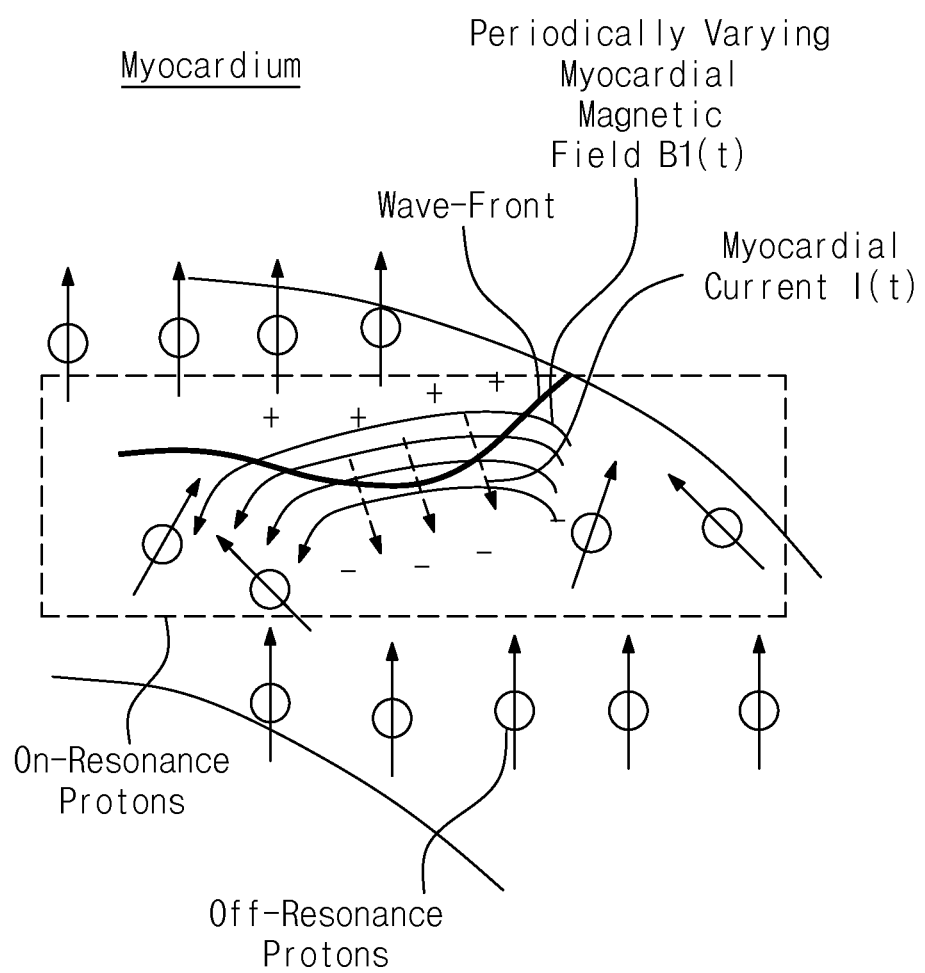
FIG. 1 illustrates a myocardial magnetic field or a biomagnetic field according to an embodiment of the present invention.

A biomagnetic field is a magnetic signal generated from person's heart, brain, spinal cord, stomach, and the like. The biomagnetic field may be measured by a high-sensitive magnetic sensor. A diagnosis using biomagnetic measurement is non-contact and non-invasive and may provide excellent time and excellent spatial resolution. Accordingly, fine variation of activity current generated in the brain or heart may be measured precisely. As a result, the biomagnetic field may be used in functional study and functional disease diagnosis of the brain, heart or the like.

In the early stage, anatomical change has been observed to diagnose and study a living person's brain. Thereafter, localization and mapping of brain functions have been tried. Afterwards, studies have been made on anatomical connectivity. In recent years, studies on brain functional connectivity are increasingly becoming important to study higher brain cognitive function. Non-invasive study instruments suitable for measurement have been developed to keep pace with interesting study topics of the brain.

Anatomical changes have been observed using X-ray, computer tomography (CT), and magnetic resonance imaging (MRI). Functional localization has been observed using magnetoencephalography (MEG), functional MRI (fMRI), and positron emission tomography (PET). Anatomical connectivity has been observed using diffusion tensor imaging (DTI). However, an instrument capable of directly observing brain functional connectivity is not developed yet.

The fMRI and the PET measure biochemical information (indirect information) following brain nerve activity, have low time resolution, and provide spatial mismatching in a practical nerve activity position.

Electroencephalogram (EEG) and the MEG are indirect estimation of position information of brain nerve current source by an inverse problem, is suitable only for activity analysis of cerebral cortex, and has lowered measurement sensitivity in nerve activity at a deep position.

According to Deep EEG and electrocorticogram (ECoG), an electrode probe is inserted into the skull by drilling the skull or an electrode is invasively attached to a surface of the brain, and only partial information may be obtained.

The DTI makes imaging of not brain function but anatomical connectivity of the brain. Therefore, a spatial connection relationship of the brain function cannot be understood directly.

An ultra-low-field magnetic resonance device according to an embodiment of the present invention may provide measurement of electrophysiological activity of human organs. An ultra-low-field brain magnetic resonance (BMR) device may directly measure brain functional connectivity. Coherent brain waves generated in association with functional connectivity of nerves may generate a coherent biomagnetic field. The coherent biomagnetic field (coherent intracerebral magnetic field) may be resonant with protons. Thus, distribution mapping of non-invasively coherent brain waves and brain functional connectivity may be measured directly.

In line with brain functional connectivity, coherent brain waves may be measured as a coherent biomagnetic field or spatial imaging of the coherent biomagnetic field while an external stimulus is applied to a part of human body or a part of human body moves. The brain functional connectivity may be extracted based on such data. When a doctor performs an operation based on the data, a part having brain functional connectivity may not be removed. Normal persons and abnormal persons may be classified by imaging the brain functional connectivity.

If an external measurement magnetic field decreases to the level of microTesla (μT), a nuclear magnetic resonance frequency of the brain may match a frequency of a coherent biomagnetic field of coherent brain waves generated by collective excitation of brain nerve current. In addition, a functional connectivity distribution of the coherent brain waves may be imaged using an MRI gradient technique. In addition, a measured signal may non-adiabatically change a measurement bias magnetic field to remove a component formed by the biomagnetic field.

In 1999, the idea of direct measuring brain nerve current using MRI was presented by Bodurka. In 2007, the test was conducted under a high magnetic field (over 1.5 T) by Parkes, et al. However, an NMR signal (2%) by change in permeability of hemoglobin is great enough to eclipse the NMR dephasing effect (2%~0.002%) by nerve current. Accordingly, there was found the fact that it was practically difficult to directly measure the brain nerve current.

If low-field NMR (1~100 μT) using an ultra high-sensitive magnetic sensor such as SQUID is used, the permeability variation effect is negligible. In addition, nuclear magnetic resonance (NMR) may be used at several kiloHertz (kHz) that is a generation frequency of a pulse train of practical brain nerves. Accordingly, NMR dephasing signal may be maximized and measured.

According to an embodiment of the present invention, instead of the brain nerve current, a coherent biomagnetic field of coherent brain waves such as spontaneous brain waves that is collective activity of brain nerves may be resonant with nuclear polarization of protons in the vicinity of a portion where the brain waves are generated. A distribution and connectivity of the brain waves may be directly imaged by measuring the resonant signal. For this reason, indirectionality and measurement limitation of fMRI, MEG or the like may be solved. Duration of coherent brain waves is several seconds, and causuality of brain functional connection may be practically studied with a phase difference of the brain waves. Thus, brain functional connectivity may be directly studied by imaging the spatial distribution of the coherent brain waves.

In a measurement method according to an embodiment of the present invention, the general artifact such as hemoglobin permeability change that occurs on conventional Tesla-level MRI may be neglected as an external magnetic field decreases to microTesla (μT).

Since a signal is measured using an induction coil in conventional NMR, an induction signal decreases when an external magnetic field is lowered to reduce a frequency. However, in a measurement method according to an embodiment of the present invention, the sensitivity of a SQUID sensor or a nuclear magnetometer type ultra high-sensitive magnetic sensor does not decrease in frequency band (10 Hz~several kHz) of external magnetic field of μT level.

Since a signal measured using MEG is several centimeter (cm) away from a signal source, the magnitude of a magnetic field is very low (100 fT~1 pT) while the magnitude of a biomagnetic field applied to protons closely near a position where nervous excitation occurs is hundreds of times higher.

Thus, the measurement method according to an embodiment of the present invention allows a nuclear magnetic resonance phenomenon to occur sufficiently.

If an oscillation frequency of the biomagnetic field issued from generation of nerve current matches a magnetic resonant frequency of nuclear polarization generated by a measurement bias magnetic field, activation of brain nerves may be directly measured from a magnetic resonance signal.

When the biomagnetic field issued from generation of coherent brain waves is maintained for a predetermined time, phase change of the magnetic resonance signal occurs due to the effect added/subtracted to/from the measurement bias magnetic field. Therefore, the activation of the brain nerves may be measured through measurement of the phase change.

Since relaxation time of protons in human body is about 1 second, nuclear polarization may be generated using a separate electromagnet with the level of tens of mT.

A brain nerve biomagnetic field oscillating in a direction perpendicular to a direction of the measurement bias magnetic field causes change in magnetization intensity and a DC magnetic field in a direction horizontal to the direction of the measurement magnetic field causes change in procession frequency of magnetization. Thus, reaction of spontaneous brain waves that are zero-mean vibration brain waves may be measured. Moreover, in case of stroke, DC-level variation of brain waves observed to be attractive in recent years may also be measured.

For example, a spatial magnetic resonance frequency may be separated by applying an external gradient magnetic field. Thus, a spatial distribution of brain nerve current may be imaged.

For example, a specific resonance region may be selected by applying an external gradient magnetic field, and imaging may be performed using frequency encoding or phase encoding by applying another external gradient magnetic field.

Since a brain magnetic resonance signal (BMR) of coherent brain waves and existing magnetoencephalography (MEG) may be measured at the same time, operating mechanism and connectivity of practical brain nerves may be studied by analyzing correlation of two signals.

An electrophysiology (EP) test is carried out to test myocardial electrical activity using a catheter. In the EP test, the catheter is inserted into the interior of human body and thus an electrode comes in contact with the endocardium to measure the myocardial electrical activity. This method is invasive and always involves the risk of surgery. Especially, a measurable part of the method is limited to the endocardium. In the case of passing through aorta and vena cava, an electrode cannot approach opposite atrium and ventricle without perforating the septum of the atrium and the ventricle. In order to place the electrode in position, a patient and a doctor have the burden of exposure to radioactivity during the treatment time. Furthermore, the method itself is unable to provide spatial information. Accordingly, means such as a magnetic position tracking device is required for spatial mapping of myocardial electrical activity.

In the case of an epicardial electrode array, there is a great burden of thoracotomy surgery and a high technology is required to attach an electrode. For this reason, the epicardial electrode array is not available in follow-up diagnosis or the like.

The spatial mapping of myocardial electrical activity using electrocardiogram (ECG) or magnetocardiogram (MCG) is current source estimation obtained by the solution of ill-posed inverse problem using a result of non-invasive measurement. Accordingly, there is a very large estimation error with respect to a deep current source or a current source whose constraint is not defined well. As a result, the ECG or the MCG is limited in clinical application.

An ultra-low-field nuclear-magnetic-resonance myocardial electrical activity detection method according to an embodiment of the present invention non-invasively measures and localizes myocardial activity which causes heart diseases such as reentry wave or ectopic excitation of heart. Thus, the detection method may provide development of new medical devices that help to research, diagnose, and treat the heart diseases.

The present invention will now be described more fully hereinafter with reference to the accompanying drawings, in which preferred embodiments of the present invention are shown. However, the present invention may be embodied in many different forms and should not be construed as limited to the embodiments set forth herein. Rather, these embodiments are provided so that this disclosure will be thorough and complete, and will fully convey the scope of the present invention to those skilled in the art. In the drawings, components are exaggerated for clarity. Like numbers refer to like elements throughout.

FIG. 1 illustrates a myocardial magnetic field or a biomagnetic field according to an embodiment of the present invention.

Figure 2:
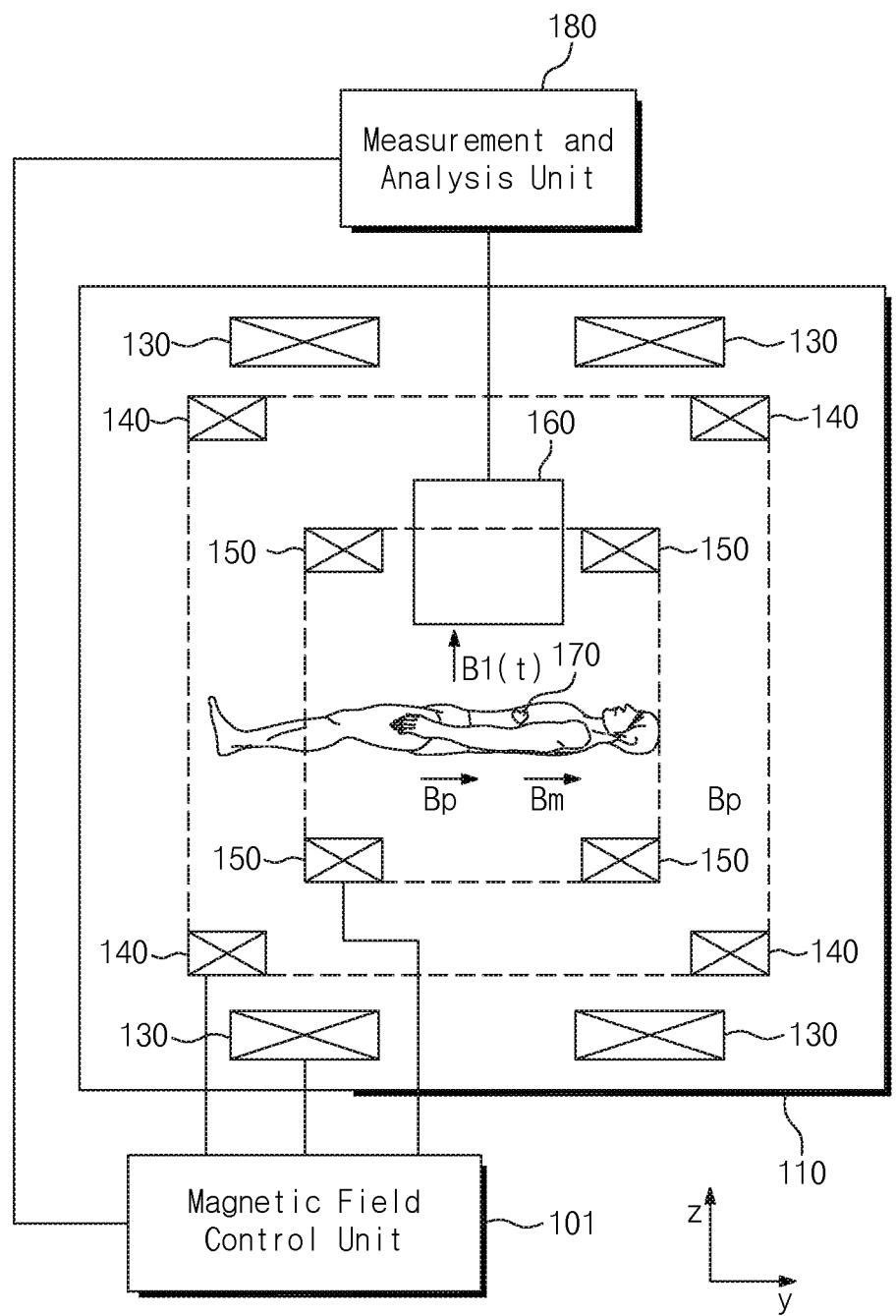
FIG. 2 illustrates an ultra-low-field nuclear magnetic resonance device using a biomagnetic field.

FIG. 2 illustrates an ultra-low-field nuclear magnetic resonance device using a biomagnetic field.

Figure 3:
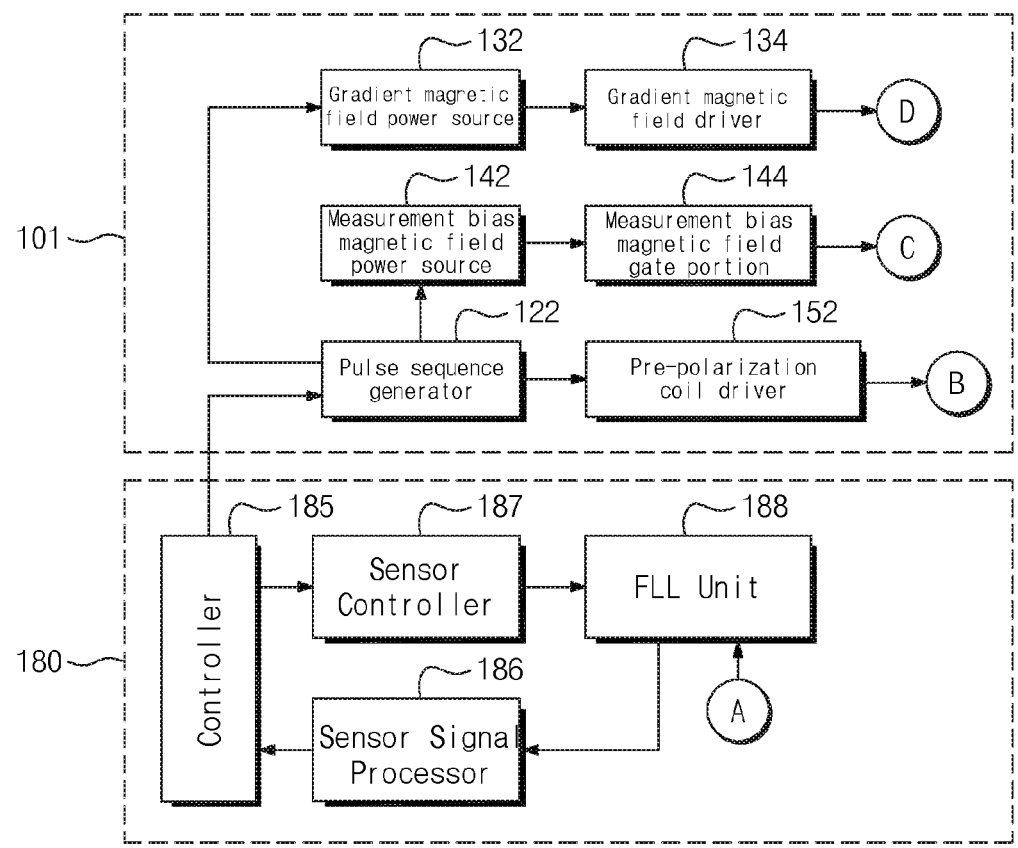
FIG. 3 is a detailed view of the ultra-low-field nuclear magnetic resonance device in FIG. 2.
Figure 3:
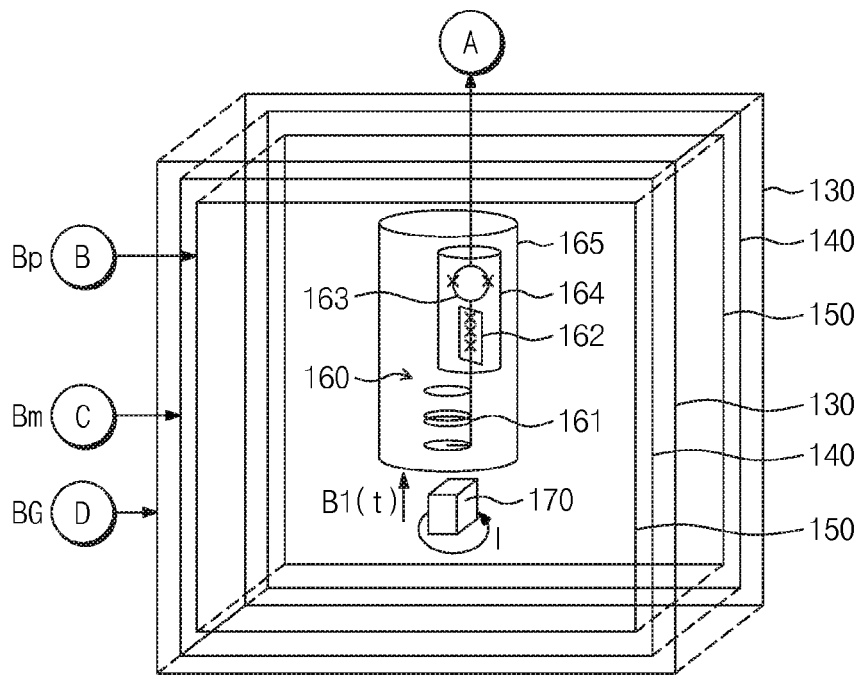

FIG. 3 is a detailed view of the ultra-low-field nuclear magnetic resonance device in FIG. 2.

Figure 4:
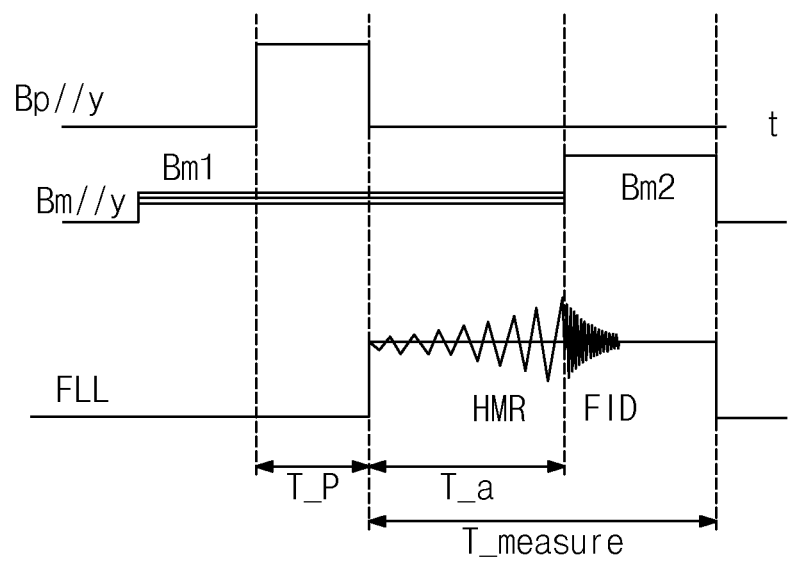
FIG. 4 shows a pulse train of the ultra-low-field nuclear resonance device in FIG. 3.

FIG. 4 shows a pulse train of the ultra-low-field nuclear resonance device in FIG. 3.

Referring to FIGS. 1 to 4, an ultra-low-field nuclear magnetic resonance measuring method may include applying a first measurement bias magnetic field with a Larmor frequency corresponding to an oscillation frequency of a periodical coherent biomagnetic field generated in association with the electrophysiological activity of human body organs; applying a second measurement bias magnetic field having the same direction and having a different magnitude than the first measurement bias magnetic field; and separating a frequency of a magnetic resonance signal generated in the human body from the oscillation frequency of the biomagnetic field by applying the second measurement bias magnetic field and measuring the magnetic resonance signal using magnetic field measuring means.

An ultra-low-field nuclear magnetic resonance measuring device includes magnetically shielding means 110, magnetic field measuring means 160 disposed adjacent to a measurement target 170 disposed inside the magnetically shielding means 110, and measurement bias magnetic field generating means 140 for applying a first measurement bias magnetic field Bm1 corresponding to a proton magnetic resonance frequency matching an oscillation frequency of a coherent biomagnetic field B1 generated in association with electrophysiological activity of human organs and successively changing the magnitude of the first measurement bias magnetic field Bm1 to apply a second measurement bias magnetic field Bm2. The magnetic field measuring means 160 measures a magnetic resonance signal generated from the measurement target 170.

The reentry excitation or ectopic excitation of the myocardium has periodical features and local and repetitive features. That is, the myocardium is excited at a specific frequency (fs) according to lesion and focus. The myocardium of a depolarized area has a potential difference with respect to that of a repolarized area. The potential difference has a wave-front and generates myocardial current I(t). The myocardial current I(t) generates a coherent biomagnetic field B1 or a myocardial magnetic field B1. A frequency (f1) of the myocardial magnetic field B1 is identical to an excitation frequency of myocardial electricity such as reentry wave or ectopic excitation. The myocardial magnetic field B1 has a strong influence on protons constituting the myocardium around the myocardial current I(t). As a distance from the myocardial current source increases, the influence is reduced.

The myocardial magnetic field of a specific oscillation frequency f1 may be utilized as B1-RF magnetic field in typical magnetic resonance imaging (MRI). The B1-RF magnetic field in the typical MRI has an RF frequency and is disposed perpendicular to an external static magnetic field. Thus, magnetization of protons precesssing along the external static magnetic field is tilted from a direction of the external static magnetic field by magnetic resonance.

Thus, if a magnetic resonance phenomenon is spatially separated and measured, a position of reentry excitation or ectopic excitation may be found out. In addition, a position and a path of brain waves may be found out.

Unlike a typical MRI device, the ultra-low-field nuclear magnetic resonance device uses an in-vivo generation phenomenon and a biomagnetic field B1 and a measurement bias magnetic field Bm having the level of microTesla ($\mu T$).

A resonance frequency depending on a magnetogyric ratio of protons of water or the like around an excited cardiogram is about 42 MHz/T. For example, let it be assumed that a frequency of reentry wave in paroxysmal atrial fibrillation desired to be searched corresponds to 42 Hz. In this case, the magnitude of an external measurement bias magnetic field Bm capable of causing magnetic resonance by absorbing the myocardial magnetic field or the biomagnetic field B1 corresponds to about 1 microTesla ($\mu T$). The biomagnetic field B1 may be generated in the z-axis direction.

Resonating protons around the myocardium, which generate a biomagnetic field B1, may create on-resonance protons. Non-resonating protons of myocardium excited at a frequency other than the frequency f1 or myocardium far away from the myocardium excited at the frequency f1 may create off-resonance protons. The magnitude of the measurement bias magnetic field Bm is as small as one-millionth of existing MRI. The magnitude of the external measurement bias magnetic field Bm is smaller than the magnitude (about 50 $\mu T$) of the earth's magnetic field. Thus, a measurement target 170 may be disposed inside the magnetically shielding means 110 to eliminate the earth's magnetic field. The magnetically shielding means 110 may be a magnetically shielded room or active magnetic shielding. The measurement bias magnetic field Bm may be generated in the y-axis direction perpendicular to the direction of the biomagnetic field (z-axis direction).

Resonating protons which are generating the biomagnetic filed B1 of oscillating frequency f1 near myocardium under the measurement bias magnetic field Bm may form on-resonance protons. In addition, myocardium which are excited of a frequency except f1 or non-resonating protons which are far away from the excited myocardium with a frequency of f1 may form off-resonance protons. The intensity of the measurement bias magnetic field Bm is as small as a 1 per million compared with that of conventional MRI. The intensity of the measurement bias magnetic field Bm is smaller than that of the magnetic field of the Earth of about 50 microTesla ($\mu T$). Therefore, the measurement target may be disposed inside a magnetic shielding means to remove the magnetic field of the Earth. The magnetic shield means may be magnetically shielded room or active magnetic shielding apparatus. The measurement bias magnetic field Bm may be formed along y direction perpendicular to the direction of the biomagnetic field (z axis).

In a weak measurement bias magnetic field Bm, it may be difficult to align proton spins. Accordingly, the practically measured intensity of a magnetic resonance signal is very low. Thus, a strong pre-polarization magnetic field Bp may be generated using pre-polarizing means 150 during a pre-determined interval T_p before measurement starts. The pre-polarization magnetic field Bp may pre-polarize a measurement target 170. Preferably, a direction of the pre-polarization magnetic field Bp may be identical to that of the measurement bias magnetic field Bm.

The protons may be aligned in a direction of the pre-polarization magnetic field Bp and the measurement target 170 may be polarized by the strong pre-polarization magnetic field Bp. The measurement target 170 may be a human body or an organ of the human body. The measurement target 170 may be the heart or brain. A magnetic resonance precession frequency of proton corresponding to the magnitude of the measurement bias magnetic field Bm is low. Accordingly, inductive measurement using a conventional coil where the intensity of a signal increases in proportion to a frequency of a measurement signal is unable to provide a signal of sufficient intensity. Thus, the high-sensitivity magnetic field measuring means 160 may be a superconducting quantum interference device (SQUID) or an optically pumped atomic magnetometer whose measurement sensitivity is independent of a signal frequency.

The bias magnetic field generating means 140 may generate the measurement bias magnetic field Bm and may be a conventional resistive coil. The bias magnetic field generating means 140 may be disposed inside the magnetic field shielding means 110. The bias magnetic field generating means 140 may arbitrarily scan the magnitude of the magnetic field. Thus, the intensity of the measurement bias magnetic field Bm may be adjusted to correspond to an excitation frequency of myocardial electricity desired to be measured. For example, the measurement bias magnetic field Bm may be applied continuously or in form of pulse in the y-axis direction.

When an oscillation frequency of the biomagnetic field B1 is 10 Hz, a frequency of a magnetic resonance signal by a first measurement bias magnetic field Bm1 is also 10 Hz. Thus, since a signal of the biomagnetic field B1 originally caused by a myocardial reentry wave (MCG signal) overlaps a signal generated in a magnetic resonance region due to magnetic resonance, they are not distinguished from each other. The measurement bias magnetic field Bm is non-adiabatically changed to overcome the above problem.

The measurement bias magnetic field Bm may include a first measurement bias magnetic field Bm1 and a second measurement bias magnetic field Bm2. The first measurement bias magnetic field Bm1 is set to be resonant with the biomagnetic field B1. The second measurement bias magnetic field Bm2 is used to change a precession frequency of resonated magnetization. Accordingly, magnetic resonance occurs during a time interval T_a after the pre-polarization magnetic field Bp turns off before the second measurement bias magnetic field Bm2 is applied. After the second measurement bias magnetic field Bm2 is applied, the magnetic resonance is removed and the precession frequency of magnetization is changed to correspond to the second measurement bias magnetic field Bm2. Thus, a signal measured during the time interval T_a includes a signal by the biomagnetic field B1 and a signal by a Magnetization component Mxz of a plane perpendicular to the first measurement magnetic field Bm1.

However, a signal measured after applying the second measurement bias magnetic field Bm2 may be separated from the signal by the biomagnetic field B1. A signal measured after applying the second measurement bias magnetic field Bm2 (FID signal) may originate in the precession of magnetization, which is tilted to a plane perpendicular to the first measurement bias magnetic field Bmf due to magnetic resonance, at a precession frequency fp2 of the second measurement bias magnetic field Bm2. Thus, the signal measured after applying the second measurement bias magnetic field Bm2 (FID signal) may be divided into a signal originating in the biomagnetic field B1 having an oscillation frequency or a magnetic resonance frequency and a magnetic resonance signal originating in precession at the precession frequency fp2 of the second measurement bias magnetic field Bm2.

The pre-polarizing means 150 may generate a pre-polarization magnetic field Bp to pre-polarize the measurement target 170. The pre-polarizing means 150 may reinforce nuclear polarization of the measurement target 170 by using dynamic nuclear polarization. The pre-polarizing means 150 may be a conventional resistive coil or a superconducting coil. The pre-polarizing means 150 may be disposed inside the magnetically shielding means 110. In addition, the pre-polarizing means 150 may be disposed inside the bias magnetic field generating means 140 while surrounding the measurement target 170. The pre-polarization magnetic field Bp may be applied in the y-axis direction by pulse.

A gradient magnetic field generating means 130 provides a gradient magnetic field to the measurement target 170. Thus, a nuclear resonance signal generated from the measurement target 170 may be localized. The gradient magnetic field generating means 130 may be a conventional resistive coil. The gradient magnetic field generating means 130 may be disposed between the measurement target 170 and the magnetically shielding means 110.

The gradient magnetic field BG may be in the y-axis direction. The gradient magnetic field generating means 130 may include first gradient magnetic field generating means to change the intensity of y-axis magnetic field depending on y-axis (dBy/dy), second gradient magnetic field generating means to change the intensity of y-axis magnetic field depending on x-axis (dBy/dx), and third gradient magnetic field generating means to change the intensity of y-axis magnetic field depending on z-axis (dBy/dz).

The magnetic field measuring means 160 is disposed adjacent to the measurement target 170 and obtains a magnetic resonance signal issued from the measurement target 170. The magnetic field measuring means 160 may measure a magnetic flux in the z-axis direction. An output signal of the magnetic field measuring means 160 is provided to a measurement and analysis unit 180. The magnetic field measuring means 160 may measure both the biomagnetic field B1 and the magnetization component resonated by the biomagnetic field B1.

The magnetic field measuring means 160 may include a magnetic flux converter 161 to sense and/or attenuate/amplify a magnetic flux, a SQUID 163 to receive an output signal of the magnetic flux converter 161 such that a magnetic field is detected to be converted into a voltage signal, and a Dewar 165 to contain a coolant.

The SQUID 163 is a type of transducer for converting variation of an external magnetic flux by combination of the Josephson effect and flux quantization that only superconductors exhibit. The SQUID 163 is a magnetic sensor that consists of one or two Josephson junctions inserted into a single superconducting loop. An RF SQUID may consist of one Josephson junction inserted into a single superconducting loop, while a DC SQUID may consist of two Josephson loops inserted into a single superconducting loop. The RF SQUID operates in the manner that an AC voltage of RF frequency band is output and its frequency varies depending on an applied flux. The DC SQUID operates in the manner that a DC voltage is generated as a function of an applied flux. The function is given in the form of a function vibration F0 ($=2.07 \times 10^{\wedge}(-15)$ Wb)) that is a quantum value of the flux. The detailed form of the flux/voltage conversion function may be decided depending on detailed structures of the DC SQUID.

The magnetic flux converter 161 may include a pick-up coil to sense a magnetic flux and convert the magnetic flux into superconducting current and an input coil to transfer the superconducting current after amplifying or attenuating the superconducting current in the form of magnetic flux. The magnetic flux converter 161 may be made of a superconductor. The pick-up coil may have a large area to detect more magnetic fluxes. The input coil may have a similar area to the SQUID 163 to focus a magnetic flux on the SQUID 163 and may be wound many times to change its amplification rate or attenuation rate. The magnetic flux converter 161 may include a magnetometer or a gradiometer. The magnetometer includes a pick-up coil consisting of a single loop, and the gradiometer includes a pick-up coil consisting of one or more loop pairs wound in opposite directions.

The SQUID may be connected to an FLL unit 188 via a conductor. The magnetic flux converter 161 may measure a magnetic flux in the z-axis direction.

There is a need for protection to stably operate the SQUID under a very larger magnetic field such as a pre-polarization magnetic field Bp. Thus, a superconducting shield is used in an ultra-low magnetic field-MRI system to protect the SQUID. However, when the entire SQUID sensor is shielded, the SQUID may not function as a magnetic field sensor. Accordingly, when shielding is performed using a superconductor, only a SQUID portion and an input coil portion of the magnetic flux converter 161 are shielded and the magnetic flux converter 161 is disposed outside the superconducting shield. In this case, the SQUID itself is protected from a strong magnetic field by the superconducting shield 164 but it is impossible to prevent current inducted from the magnetic flux converter 161 from being applied to the SQUID. Therefore, a current limiter 162 may be disposed in an ultra-low magnetic field-NMR system to prevent overcurrent inducted from a pick-up coil from being applied to the SQUID.

The measurement and analysis unit 180 may provide a frequency and a position of reentry excitation in paroxysmal atrial fibrillation by using the magnetic resonance signal.

The measurement and analysis unit 180 may include a flux-locked loop (FLL) unit 188 linearizing a voltage signal of the SQUID 163 and providing the linearized voltage signal as a voltage signal in proportion to a detected magnetic field, a sensor signal processor 186 processing the linearized voltage signal to remove a noise and amplify, and a sensor controller 187 providing a control signal to the FLL unit 188.

The FLL unit 188 may include an input terminal to receive an output signal of the SQUID 163, an integrator, a feedback-type linearization circuit, a feedback coil, and the like. The FLL unit 188 may convert the change amount of a flux into a voltage signal having a much wider range than a flux quantum value FO before outputting the voltage signal.

The pulse sequence generator 122 receives the control signal from the controller 185 to provide a pulse sequence to a pre-polarization coil driver 152, a measurement bias magnetic field power source 142, and a gradient magnetic field power source 132.

A magnetic field control unit 101 may apply various magnetic fields to the measurement target 170 in synchronization with the measurement and analysis unit 180. The magnetic field control unit 101 may control the pre-polarization generating means 150, the bias magnetic field generating means 140, and the gradient magnetic field generating means 130 according to a series of orders.

The magnetic field control unit 101 includes the pre-polarization coil driver 152 that intermittently applies current to the pre-polarization means 150 to generate a prepolarization magnetic field Bp. The measurement bias magnetic field generating means 140 applying a measurement bias magnetic field Bm to the measurement target 170 is connected to a measurement bias magnetic field gate portion 144. The measurement bias magnetic field gate portion 144 is connected to the measurement bias magnetic field power source 142.

The gradient magnetic field generating means 130 is connected to the gradient magnetic field driver 134, and the gradient magnetic field driver 134 is connected to the gradient magnetic field power source 132.

The measurement and analysis unit 180 may process a magnetic resonance signal (FID signal or gradient echo signal) to extract a frequency component corresponding to the second measurement bias magnetic field. The frequency component corresponding to the second measurement bias magnetic field may identify a resonant region that resonates with the coherent biomagnetic field B1 of the measurement target.

The gradient magnetic field generating means 130 may apply a gradient magnetic field BG to the measurement target 170. The gradient magnetic field driver 134 supplies current to the gradient magnetic field generating means 130 to apply the gradient magnetic field BG to the measurement target 170. The gradient magnetic field power source 132 may supply power to the gradient magnetic field driving part 134. The gradient magnetic field power source 132 receives a pulse sequence from the pulse sequence generator 122 to supply power to the gradient magnetic field driver 134. The gradient magnetic field generating means 130 may generate gradient magnetic fields dBy/dy, dBy/dz, and dBy/dx.

The measurement bias magnetic field generating means 140 may generate a spatially uniform and low measurement bias magnetic field Bm. The measurement bias magnetic field generating means 140 may be connected to the measurement bias magnetic field power source 142. The measurement bias magnetic field gate portion 144 may adjust current applied to the measurement bias magnetic field generating means 140 to intermittently generate the measurement bias magnetic field Bm.

The pulse sequence generator 122 may generate a pulse sequence and provide the pulse sequence to the pre-polarization coil driver 152, the measurement bias magnetic field power source 142, and the gradient magnetic field power source 132 to obtain an FID signal or a gradient echo signal.

The controller 185 may process a signal of the sensor signal processor 186 and control the pulse sequence generator 122 and the sensor controller 187.

An optical solid-state relay (SSR) may be used as a switch to turn on and turn off a pre-polarization magnetic field Bp, a measurement bias magnetic field Bm, and a gradient magnetic field BG. While the SSR is turned off, the pre-polarization means 150, the measurement bias magnetic field generating means 140, and the gradient magnetic field generating means 130 may be completely open-circuited from a current source. A TTL signal for driving the SSR may be applied by means of optical communication. Thus, all electrical connections having an influence on the measurement and analysis unit 180 or the magnetic field measuring means 160 may be removed.

According to a modified embodiment of the present invention, the first measurement bias magnetic field may be scanned to match an oscillation frequency of the biomagnetic field B1 with a resonant frequency of the first measurement bias magnetic field. The amplitude of an HMR signal obtained during application of the first measurement bias magnetic field may increase due to magnetic resonance. An FID signal obtained after application of the second measurement bias magnetic field may decrease with the lapse of time from the termination of magnetic resonance.

The HMR signal and the FID signal may be Fourier-transformed to be divided into a frequency component by the biomagnetic field B1 and a frequency component by magnetic resonance.

According to a modified embodiment of the present invention, the measurement target may be one-dimensionally, two-dimensionally, and three-dimensionally imaged by applying a conventional space imaging technique.

According to a modified embodiment of the present invention, a method for measuring brain functional connectivity is characterized in that a magnetic resonance signal generated from protons resonated by a coherent biomagnetic field of a specific frequency in a person's brain is measured using an ultra-low nuclear resonance apparatus and is spatially imaged to detect brain functional connectivity.

A method for measuring brain functional connectivity according to a modified embodiment of the present invention is characterized in that a magnetic resonance signal generated from protons resonated by a coherent biomagnetic field of a specific frequency in a person's brain is measured using an ultra-low nuclear resonance apparatus and is spatially imaged to detect brain functional connectivity. The method includes applying a first measurement bias magnetic field a Larmor frequency corresponding to an oscillation frequency of a brainwave magnetic field generated in association with brain functional connectivity, applying a second measurement bias magnetic field having the same direction as the first measurement bias magnetic field and having a different magnitude than the first measurement bias magnetic field, and separating a frequency of a magnetic resonance signal generated in the brain from the oscillation frequency of the brainwave magnetic field by applying the second measurement bias magnetic field and measuring the magnetic resonance signal using magnetic field measuring means.

Figure 5:
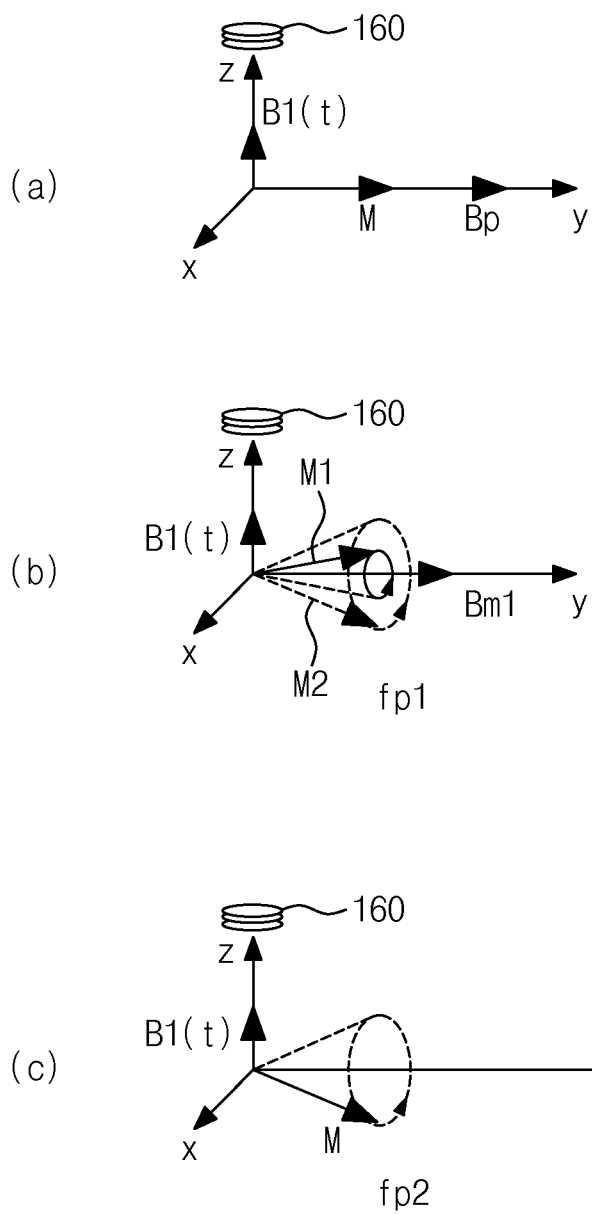
FIG. 5 illustrates the operation principle of an ultra-low-field nuclear resonance device according to an embodiment of the present invention.

FIG. 5 illustrates the operation principle of an ultra-low-field nuclear resonance device according to an embodiment of the present invention.

Referring to FIG. 5, high-sensitive magnetic field measuring means 160 is disposed to be sensitive to a magnetic field parallel to the z-axis direction on the basis of a Cartesian coordinate system. Both a pre-polarization magnetic field Bp generated by pre-polarizing means and a measurement bias magnetic field Bm generated by measurement bias magnetic field generating means may be applied to be parallel to the y-axis direction. In this case, nuclear spin of a measurement target is aligned in the y-axis direction to generate magnetization M. The measurement starts shortly after the pre-polarization magnetic field is turned off.

In this case, the generated magnetization M rotates on y-axis that is a direction of a first measurement bias magnetic field Bm1. If there is no myocardial activity causing magnetic resonance, there is no magnetization component Mz in the z-axis direction from the start. Therefore, a magnetic field in the z-axis direction is not changed and a signal is not measured in spite of rotation of the magnetization M.

However, when a reentry wave is periodically generated at a magnetic resonance frequency of the first measurement bias magnetic field Bm1 by myocardial abnormality and a direction of a myocardial magnetic field having an oscillation frequency of alternating current generated from change of cardiac current is the z-axis direction, the magnetization M aligned in the y-axis direction by a magnetic resonance phenomenon is tilted in the x-axis or z-axis direction. The tilted magnetization M rotates on the y-axis that is a direction of the first measurement bias magnetic field Bm1. A frequency of the precession is fp1. Thus, a z-axis direction component of varying magnetization is formed to generate a magnetic field in the z-axis direction. The magnetic field in the z-axis direction may be measured by the high-sensitive magnetic field measuring means 160.

An oscillation frequency f1 of a myocardial magnetic field and a frequency fp1 of a magnetic resonance signal are identical to each other. Since the magnetic field resonance signal overlaps a myocardial magnetic field signal where a myocardial reentry wave is generated, they are not identified. In order to overcome this problem, the measurement bias magnetic field is non-adiabatically changed.

That is, the first measurement bias magnetic field changes into a second measurement bias magnetic field having a different magnitude. Thus, a frequency of precession changes into fp2. For this reason, a signal magnetically resonated from a measured signal has the frequency fp2 and a biomagnetic field signal has the frequency fp1. As a result, the magnetically resonated signal may be identified.

Myocardial abnormality may be directly measured by adjusting or scanning an applied measurement bias magnetic field Bmf according to a direction or a frequency of myocardial electrical activity desired to be measured. Magnetic resonance imaging (MRI) techniques using a conventional gradient magnetic field may be utilized to obtain spatial location information.

Atrial fibrillation, which is a kind of atrial arrhythmias, results from generation of a reentry wave that is caused by aging or deformation of an atrial myocardium. In particular, when seeking its causal part where a high-frequency f wave (periodical waveform) comes out through a catheter electrode, treatment is carried out using RF ablation or freezing technique. However, it is difficult and it takes a lot of time to carry out seeking through one-by-one contact using a probe. Moreover, an invasive test is a burden on checking prognosis after surgery.

If the configuration of the present invention is applied to this case, a point where a myocardial high frequency fm is generated may be imaged very safely and effectively.

Measurement possibility of heart magnetic resonance (HMR) was verified through a simulation. The simulation started from configuring a myocardial reentry wave to some degree of forming a signal size of atrial arrhythmias f-wave that has been practically measured in a magnetocardiogram study.

Figure 6:
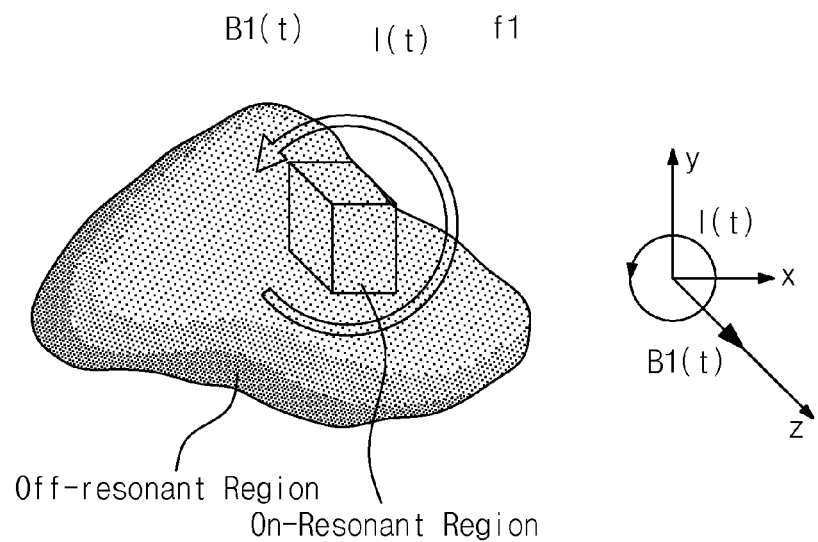
FIG. 6 shows a situation of simulation.

FIG. 6 shows a situation of simulation.

Referring to FIG. 6, there was assumed a myocardial reentry wave that circulates counterclockwise on a surface of myocardium at a frequency of 10 Hz. Thus, the myocardial reentry wave generates coherent biological current. The biological current rotates counterclockwise on the xy plane. Thus, a biomagnetic field is generated in the z-axis direction. A frequency of the biomagnetic field is f1. A coherent biomagnetic field to generate a myocardial reentry wave was calculated using a heart and thorax conductor model by a boundary element method. This makes it possible to calculate respective biomagnetic fields generated by the myocardial reentry wave at respective voxels in the volume near the myocardial reentry wave. The calculated value of the biomagnetic field is about 100 pT at the myocardium that is about 1 mm away from the myocardial reentry wave. Thus, the magnitude of an RF magnetic field was great enough to tilt magnetization under various time constant conditions used in the test. Dynamics of magnetizations at the respective voxels by the generated biomagnetic field may be calculated using Bloch equation.

A sampling rate of the simulation was 1 kHz. The volume established by the voxels used in the calculation is an internal space of a cube whose one side is 20 mm in the center of the myocardial reentry wave. It was assumed that magnetization of heart tissue was about 30 percent of water. A magnetization value in calculation of a voxel was defined compared with a measurement NMR signal size of water in an existing ultra-low magnetic field. It was assumed that the magnitude of a pre-polarization magnetic field under the simulation test conditions was 200 mT. Once the pre-polarization magnetic field is turned off, there is no strong magnetic field component to generate magnetization. Therefore, only relaxation of the magnetization occurs. At this point, both T1 (spin-lattice relaxation time) and T2 (spin-spin relaxation time) were calculated under 1 second. A magnetic resonance field for a tissue excited at 10 Hz is 235 nT. While the first measurement bias magnetic field Bm1 of 235 nT is applied along the y-axis parallel to the pre-polarization magnetic field Bp, a magnetic field was calculated at a position of a SQUID sensor. The magnetic field is generated when magnetization of each voxel reacts with a change of peripheral magnetic fields (a measurement magnetic field and an biomagnetic field).

Since a frequency of a generated magnetic resonance signal is also 10 Hz, the magnetic resonance signal overlaps a magnetocardiogram signal where a myocardial reentry wave is originally generated. Therefore, the two signals are not identified. In order to overcome this problem, a measurement bias magnetic field is non-adiabatically changed. That is, in this simulation, a first measurement bias magnetic field Bm1 of 235 nT (10 Hz) may change into a second measurement bias magnetic field Bm2 of 2,350 nT (100 Hz) which is 10 times greater than 235 nT (10 Hz) of the first measurement bias magnetic field Bm1.

Then, a free induction decay (FID) signal may be measured. Thus, an HMR signal may be separated from an original magnetocardiogram or biomagnetic signal. In addition, the HMR signal is limited to a specific measurement frequency (100 Hz). Thus, ease of measuring a signal to a system noise may be significantly improved by reducing measurement bandwidth.

Periodical reentry oscillation at a myocardium in a counterclockwise direction generates biomagnetic fields oscillating in a region of interest (ROI). When a Larmor frequency corresponding to the measurement bias magnetic field Bm matches a frequency of the biomagnetic field Bm, magnetization generated by the pre-polarization magnetic field in the region of interest starts to be tilted by magnetic resonance.

A z component of the magnetization M increases with magnetic resonance. The z component of the magnetization M is detected by magnetic field measuring means such as a SQUID. A signal detected by the SQUID includes a biomagnetic field component formed by a myocardial reentry wave. Thus, the measurement bias magnetic field temporarily changes from a first measurement bias magnetic field to a second measurement bias magnetic field to separate a biomagnetic field component from the detected signal. Accordingly, magnetic resonance conditions established by the biomagnetic field are broken. As a result, since the z component of the magnetization M does not satisfy the magnetic resonance conditions, the z component is reduced by spin-spin interaction. In addition, when the magnitude of the second measurement bias magnetic field Bm2 is 10 times greater than that of the first measurement bias magnetic field Bm1, a frequency of precession in a direction of the second measurement bias magnetic field Bm2 increases by 10 times.

Figure 7:
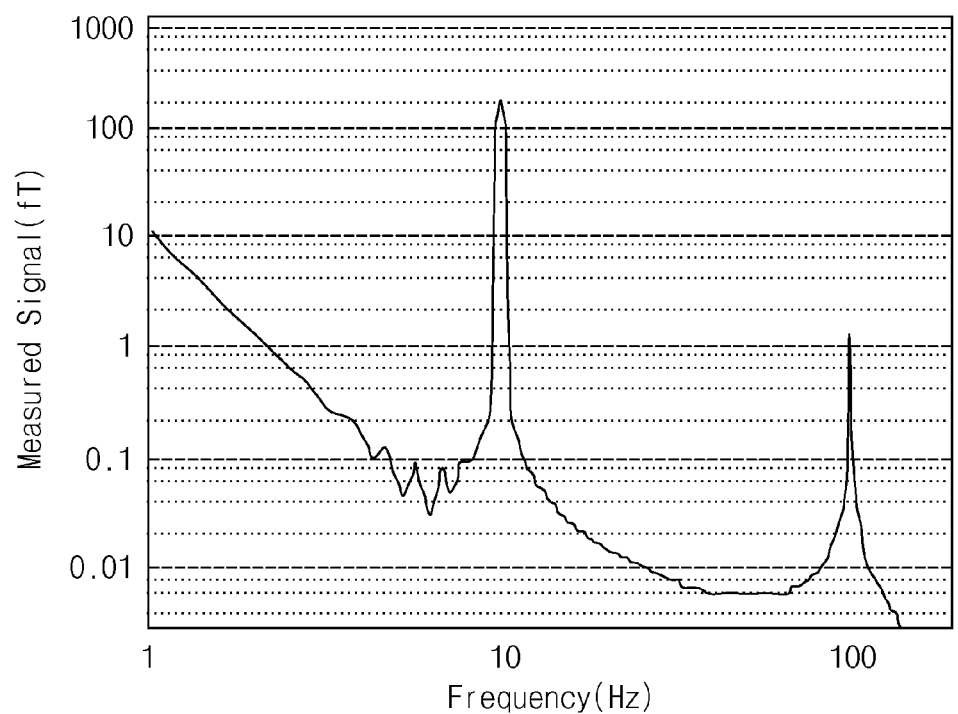
FIG. 7 is a graph in which a 10 Hz component is an MCG signal of reentry excitation and a 100 Hz signal is an FID signal of HMR.

Referring to FIG. 7, a 10 Hz component is a magnetocardiogram (MCG) signal of reentry excitation, and a 100 Hz signal is an FID signal of HMR.

Figure 8:
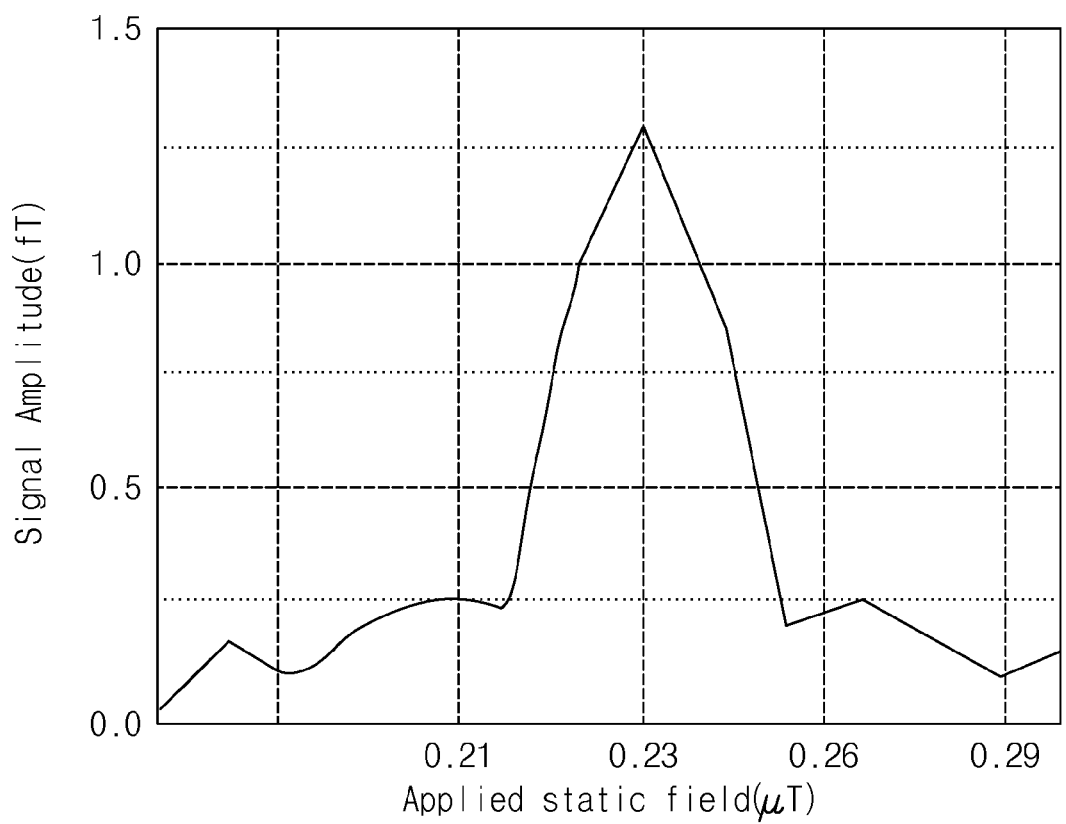
FIG. 8 is a graph of a frequency selectivity of HMR.

FIG. 8 is a graph of a frequency selectivity of HMR.

Referring to FIG. 8, frequency selectivity of HMR changes the magnitude of a first measurement bias magnetic field Bm1, and an FID signal is measured under a fixed second measurement bias magnetic field (corresponding to 100 Hz). Thus, amplitude of a 100 Hz component depending on the magnitude of the first measurement bias magnetic field Bm1 is displayed.

Reentry frequency selectivity exhibits resolution of 1 Hz, and a corresponding magnetic field is about 20 nT. In a magnetically shielded room, non-uniformity of a magnetic field is about 20 nT/10 cm. Accordingly, it is expected that magnetic field non-uniformity under a practically measured situation will not have an influence on frequency selectivity.

Intensity of an HMR signal is several fT. In the currently developed highest-level technology, noise of a SQUID and noise of a Dewar are all in the level of sub-fT/vHz. According to the measuring method of the present invention, measured bandwidth may be limited to width of a signal. Accordingly, it is expected that a signal-to-noise ratio (SNR) will be between several and several dozen degrees under the assumption that measured bandwidth is between about 0.1 Hz and about 1 Hz. As a result, the HMR signal may be measured.

Figure 9:
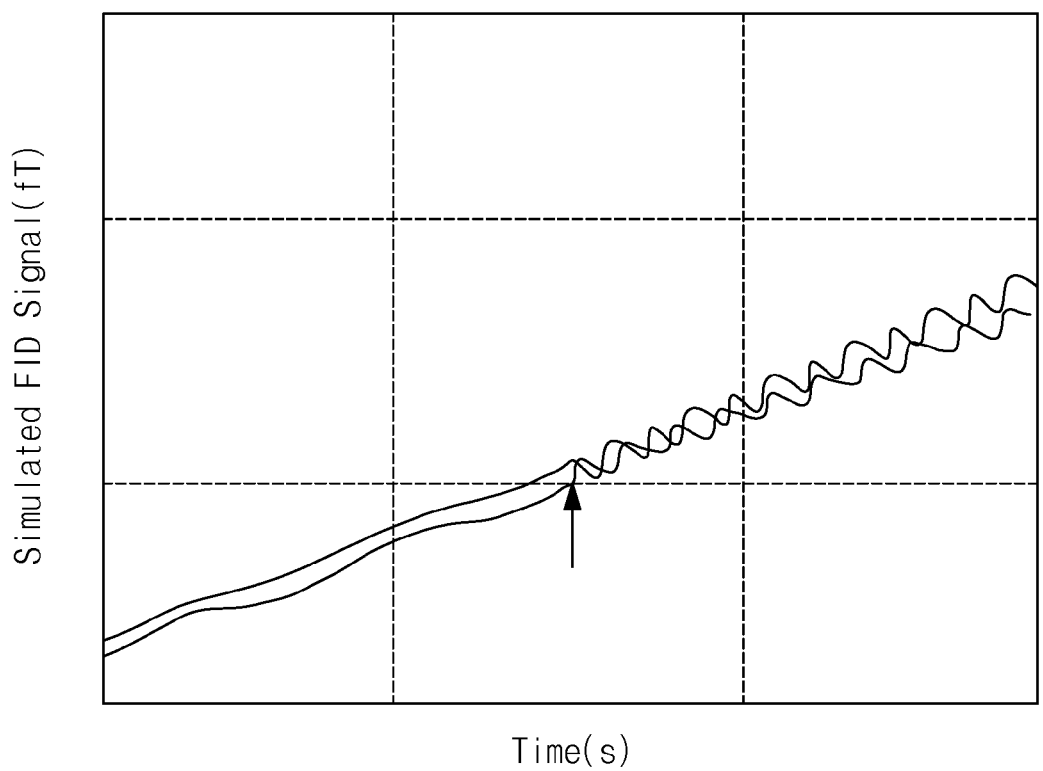
FIG. 9 is a graph of a simulation result showing the magnitude of a magnetic field where a magnetization behavior at each voxel is measured by a SQUID sensor.

FIG. 9 is a graph of a simulation result showing the magnitude of a magnetic field where a magnetization behavior at each voxel is measured by a SQUID sensor.

Referring to FIG. 9, in the simulation, a SQUID sensor is disposed above 2 cm from a chest surface, and myocardium is disposed at the depth of 4 to 6 cm from the chest surface. A first measurement bias magnetic field Bmf is in the y-axis direction, and a biomagnetic field B1 is in the z-axis direction. Before variation of a non-adiabatic measurement bias magnetic field, a gradually increasing measurement signal component may be formed while magnetization is titled in the z-axis direction due to HMR effect. An arrow point is a change point of a measurement bias magnetic field. At the arrow point, a measurement magnetic field changes from a first measurement magnetic field to a second measurement magnetic field. Magnetization generated from that point produces free induction decay (FID) while generating a signal of 100 Hz.

According to the present invention, a generation or occurrence position of a cardiac reentry wave or ectopic excitation may be found out very accurately using a non-invasive method. Therefore, the present invention may be applied to safe and convenient medical diagnosis. Long-time dangerous surgery and radiation exposure of patents as well as doctors may be reduced. Since the technology may be used not only in diagnosis for treatment but also in prognosis observation after treatment without burdens, it may be applied to development of novel and innovative medical equipments.

FIGS. 10A to 10D illustrate a pulse train according to another embodiment of the present invention.

Referring to FIGS. 10A to 10D, a pre-polarization magnetic field is applied in the y-axis direction for predetermined time T_BP. The pre-polarization magnetic field may pre-polarize a measurement target. A first measurement bias magnetic field is applied for constant time. After the pre-polarization magnetic field is removed, a biomagnetic field may provide magnetic resonance due to the first measurement bias magnetic field.

In order to generate a gradient echo signal, a first gradient echo magnetic field Ge1 and a second gradient echo magnetic field Ge2 may be successively applied. The first gradient echo magnetic field Ge1 and the second gradient echo magnetic field Ge2 may generate gradient magnetic fields of opposite directions. More specifically, the first gradient echo magnetic field Ge1 may form a positive dBy/dy component, and the second gradient echo magnetic field Ge2 may form a negative dBy/dy component. If the second gradient echo magnetic field Ge2 of opposite polarity to the first gradient magnetic field Ge1 is applied at the end point of the first gradient echo magnetic field Ge2, spins that are being dephased are refocused by a gradient magnetic field of opposite polarity. Thus, a gradient echo signal may be generated.

Applying a gradient magnetic field for obtaining an image in a nuclear magnetic resonance measuring method may be divided into two steps.

An ultra-low-field nuclear magnetic resonance measuring method may include setting up a resonance region using a gradient magnetic field and spatial imaging using the gradient magnetic field. The gradient magnetic field may include a resonance region selection gradient magnetic field and an encoding gradient magnetic field.

[1] Resonance Region Setup Period (T_a)

Resonance region selection gradient magnetic fields Gr1, Gr2, and Gr3 may include at least one of a first resonance region selection magnetic field Gr1, a second resonance region selection magnetic field Gr2, and a third resonance region selection magnetic field Gr3. The first resonance region selection magnetic field Gr1, the second resonance region selection magnetic field Gr2, and the third resonance region selection magnetic field Gr3 may provide gradient magnetic fields with respect to different directions. The resonance region selection gradient magnetic fields Gr1, Gr2, and Gr3 may be applied before the second measurement bias magnetic field Bm2 is applied.

The magnitudes of the resonance region selection magnetic fields Gr1, Gr2, and Gr3 may be scanned such that the sum of the magnitudes of the resonance region selection magnetic fields Gr1, Gr2, and Gr3 and the magnitude of the first measurement magnetic field Bm1 corresponds to an oscillation frequency of a coherent biomagnetic field B1.

More specifically, when imaging an alpha wave (α-wave) of a parietal region, it is necessary to understand a frequency fα of the α-wave and/or a generation position of the α-wave.

In order to know the frequency fα of the α-wave, it is necessary to scan the first measurement bias magnetic field Bm1 that is spatially uniform.

Alternatively, the resonance region selection magnetic fields Gr1, Gr2, and Gr3 and the first measurement bias magnetic field Bm1 may be simultaneously applied without scanning the first measurement bias magnetic field Bm1 that is spatially uniform. Thus, magnetic fields may have spatially different magnitudes. For this reason, magnetic resonance may occur in a magnetic field corresponding to frequency fα of the α-wave in a predetermined region. The first resonance region selection gradient magnetic field Gr1 may have a dBy/dy component. The second resonance region selection gradient magnetic field Gr2 may have a dBy/dx component. The third resonance region selection gradient magnetic field Gr3 may have a dBy/dz component.

For example, if a 10 Hz α-wave of a parietal region is imaged, 235 nT corresponding to 10 Hz is applied to the center of the parietal region and another magnetic field is applied to a peripheral part of the parietal region by spatial gradient. Accordingly, magnetic resonance for brain activity of 10 Hz occurs only in the center of the parietal region.

More specifically, the 10 Hz α-wave may generate a coherent biomagnetic field of y-axis direction in the parietal region. The first measurement bias magnetic field Bm1 and the gradient magnetic fields Gr1, Gr2, and Gr3 are applied in the y-axis direction. A magnetic field is applied in the y-axis direction such that the sum of the first measurement bias magnetic field Bm1 and the gradient magnetic field is 235 nT corresponding to 10 Hz in the center of the parietal region. Thus, magnetic resonance occurs in the parietal region, and a component lying on an x-y plane is formed only at an occurrence portion of the magnetic resonance.

[2] Generated Signal Spatial Imaging Period (T_c)

A distribution of resonating nucleuses where an x-z component is formed is spatially imaged.

An encoding gradient magnetic field Gen may be applied after the second measurement bias magnetic field Bm2 is applied. The encoding gradient magnetic field Gen may include at least one of a first encoding gradient magnetic field Gen1 and a second encoding gradient magnetic field Gen2. The encoding gradient magnetic field Gen may perform at least one of frequency encoding and phase encoding.

The first measurement bias magnetic field Bm1 may change into the second measurement bias magnetic field Bm2. Thus, magnetic resonance conditions are not satisfied in the parietal region.

If the second measurement bias magnetic field and a y-axis magnetic field (gradient magnetic field) having a spatially different magnitude than the second measurement bias magnetic field are applied at the same time, the resonating nucleuses are generating signals of different frequency with respect to a space. The first encoding gradient magnetic field Gen1 may have a magnitude of dBy/dx and may be in the y-axis direction, and the second encoding gradient magnetic field Gen2 may have a magnitude of dBy/dz and may be in the y-axis direction.

While a bias magnetic field and a gradient magnetic field exist, a signal has a different frequency (for example 100 Hz) than a resonance region setup period T_a in which 10 Hz resonance occurs. If a gradient etch signal obtained at this point is fast-Fourier-transformed, a frequency-dependent signal distribution may be shown. As a result, since the frequency corresponds to another position, the signal may be spatially imaged.

Figure 11:
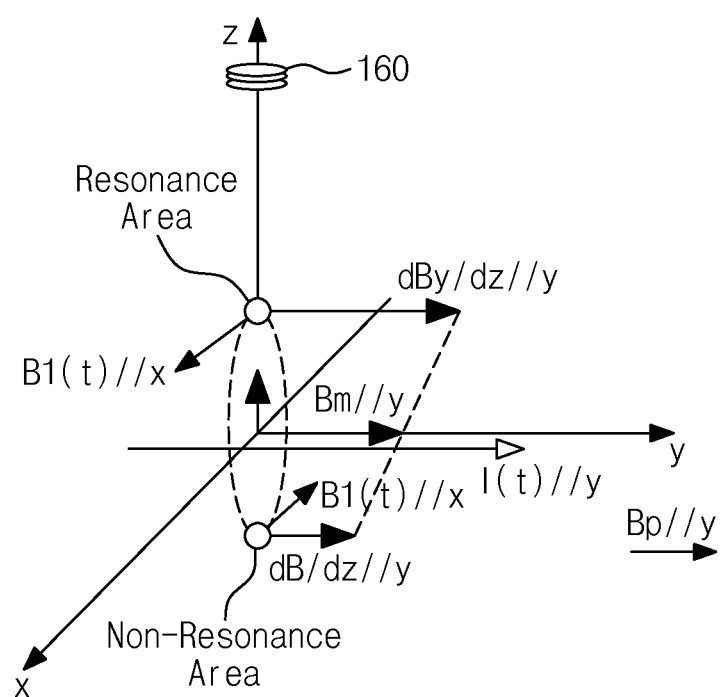
FIG. 11 illustrates a nuclear magnetic resonance measuring method according to another embodiment of the present invention.

FIG. 11 illustrates a nuclear magnetic resonance measuring method according to another embodiment of the present invention.

Referring to FIG. 11, according to a modified embodiment of the present invention, a resonance region setup step is distinguished from an existing imaging method. For example, when a spontaneous brain wave current source passes, a biomagnetic field B1 of an opposite direction is generated at the top and bottom of the current source.

That is, directions of nuclear magnetization lying due to a resonance phenomenon are opposite at the top and bottom of the current source. Thus, phases of a magnetic field generated when rotating on the measurement bias magnetic field Bm of the y-axis direction are opposite to each other. For this reason, signals measured at a position of a SQUID sensor are offset with each other. Practically, magnetically resonated magnetization at the top of the current source comes closer to the SQUID sensor to be more measured than at the bottom of the current source. Thus, most signals generated by the magnetically resonated magnetization are lost, and only a few signals are measured.

However, if only nucleuses at the top of the current source are spatially distinguished through a resonance region selection gradient magnetic field to resonate with a biomagnetic field (e.g., 0.235 nT at the top and 0.1 nT at the bottom), nucleuses at the bottom of the current source do not resonate. Thus, an x-z component of the magnetization is not formed in a bottom region. For this reason, magnetization above the formation position may be purely measured without decay. When a position of the current source is not known, position division may be performed by a repeated method.

Figure 12:
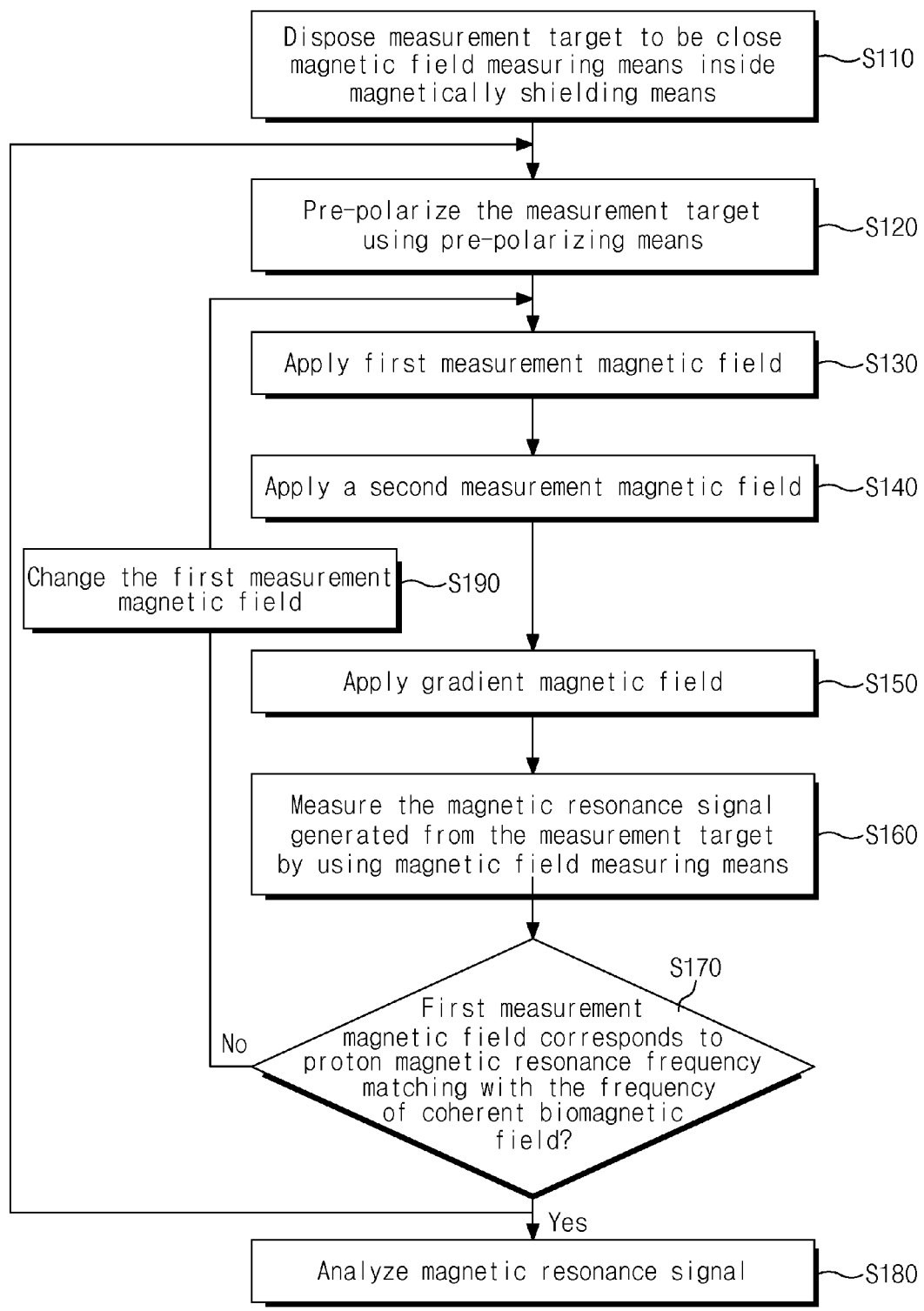
FIGS. 12 and 13 are flowcharts summarizing a nuclear magnetic resonance measuring method according to an embodiment of the present invention.
Figure 13:
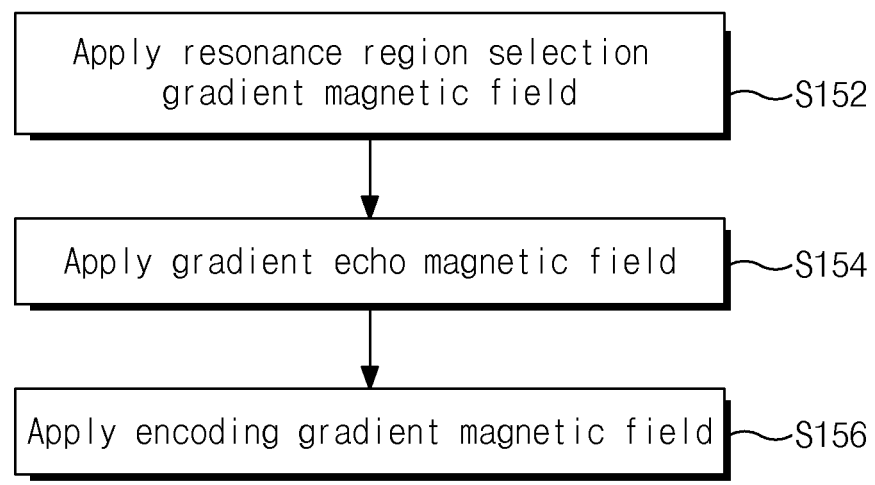

FIGS. 12 and 13 are flowcharts summarizing a nuclear magnetic resonance measuring method according to an embodiment of the present invention.

Figure 10A:
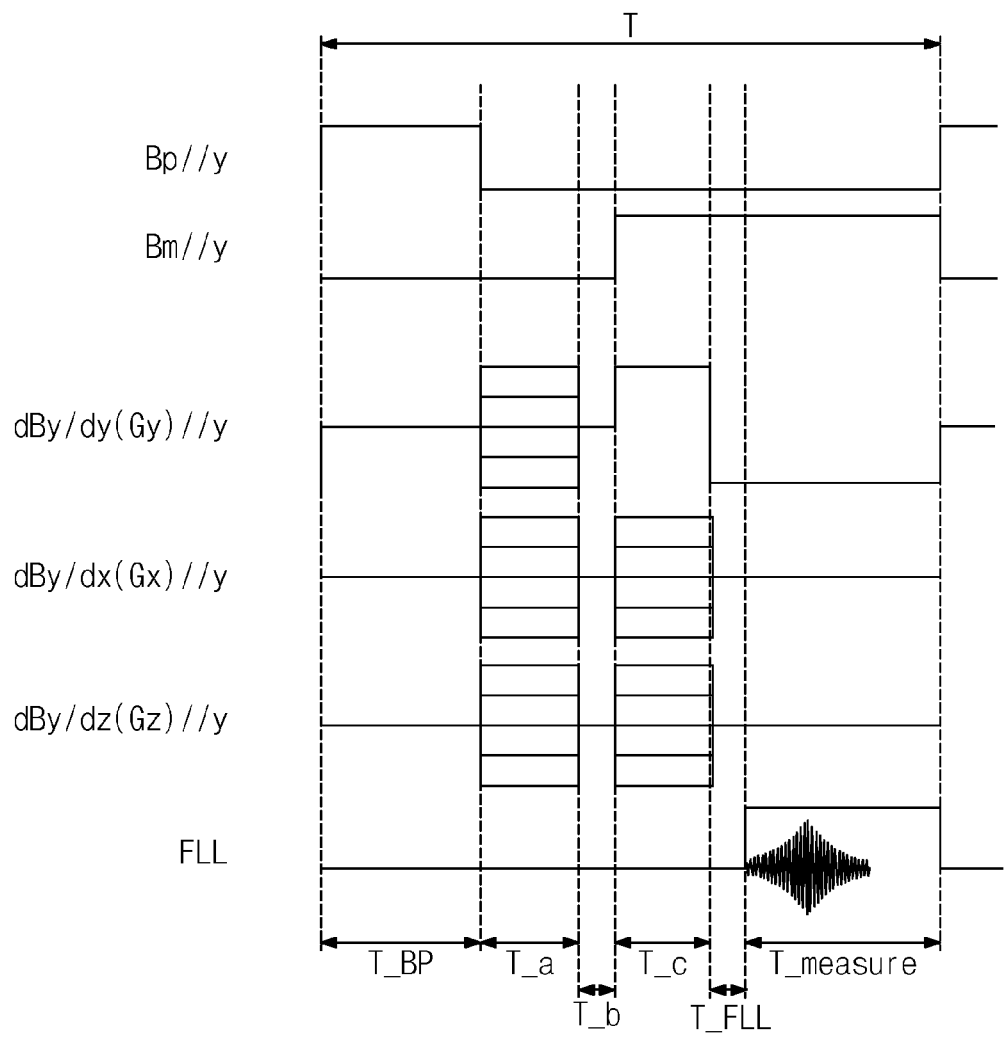
FIGS. 10A to 10D illustrate a pulse train according to another embodiment of the present invention.
Figure 10B:
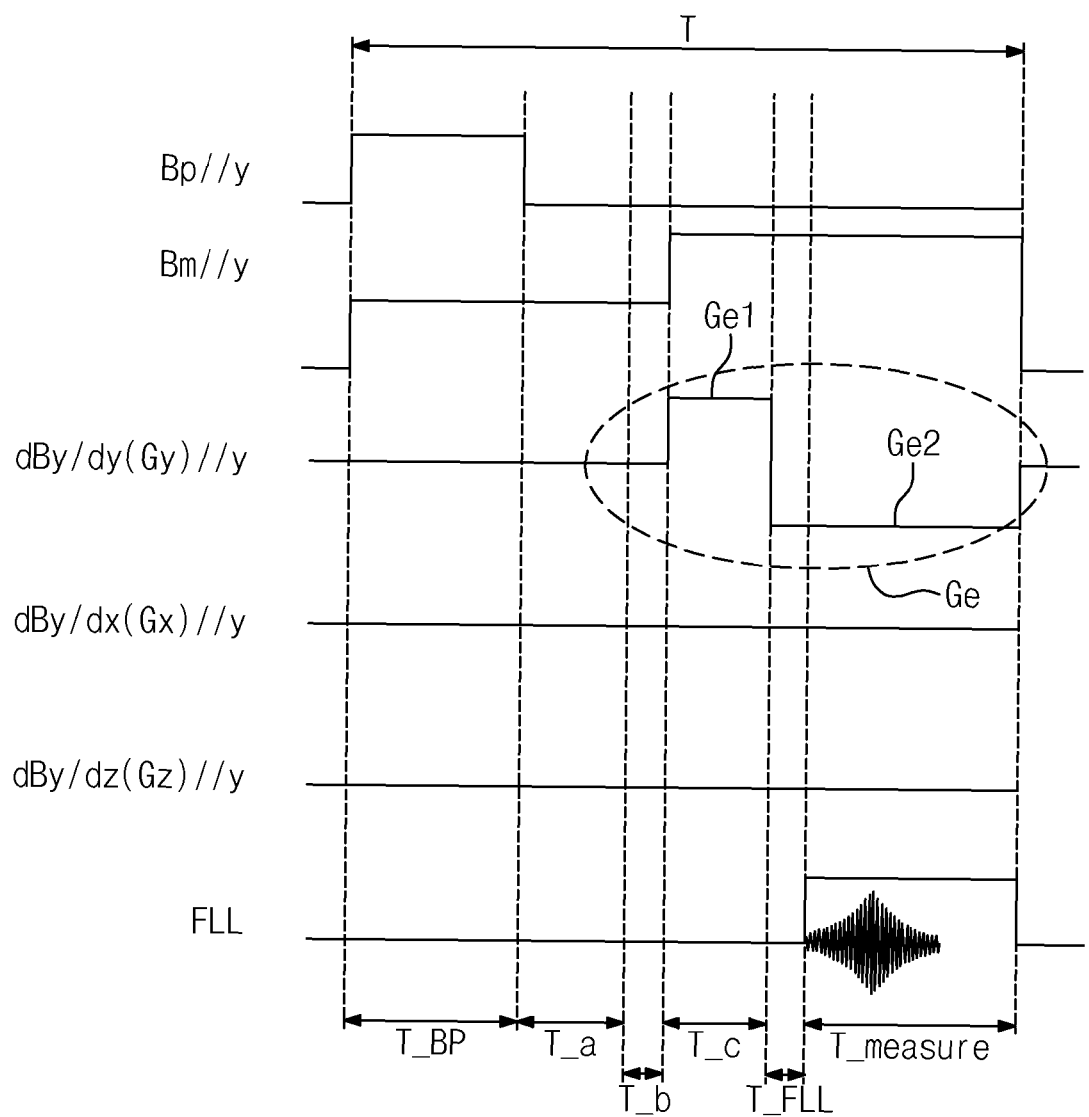
Figure 10C:
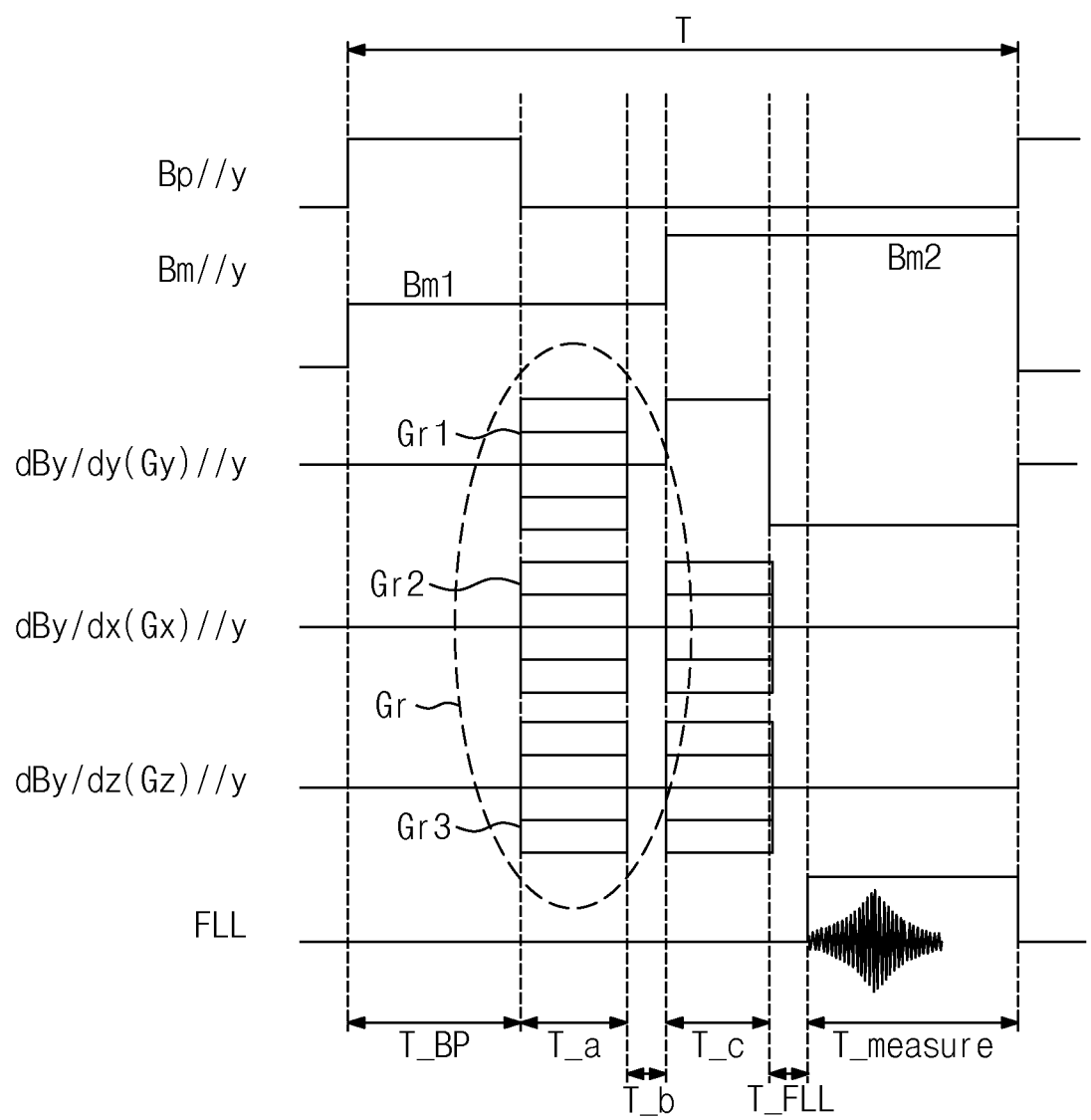
Figure 10D:
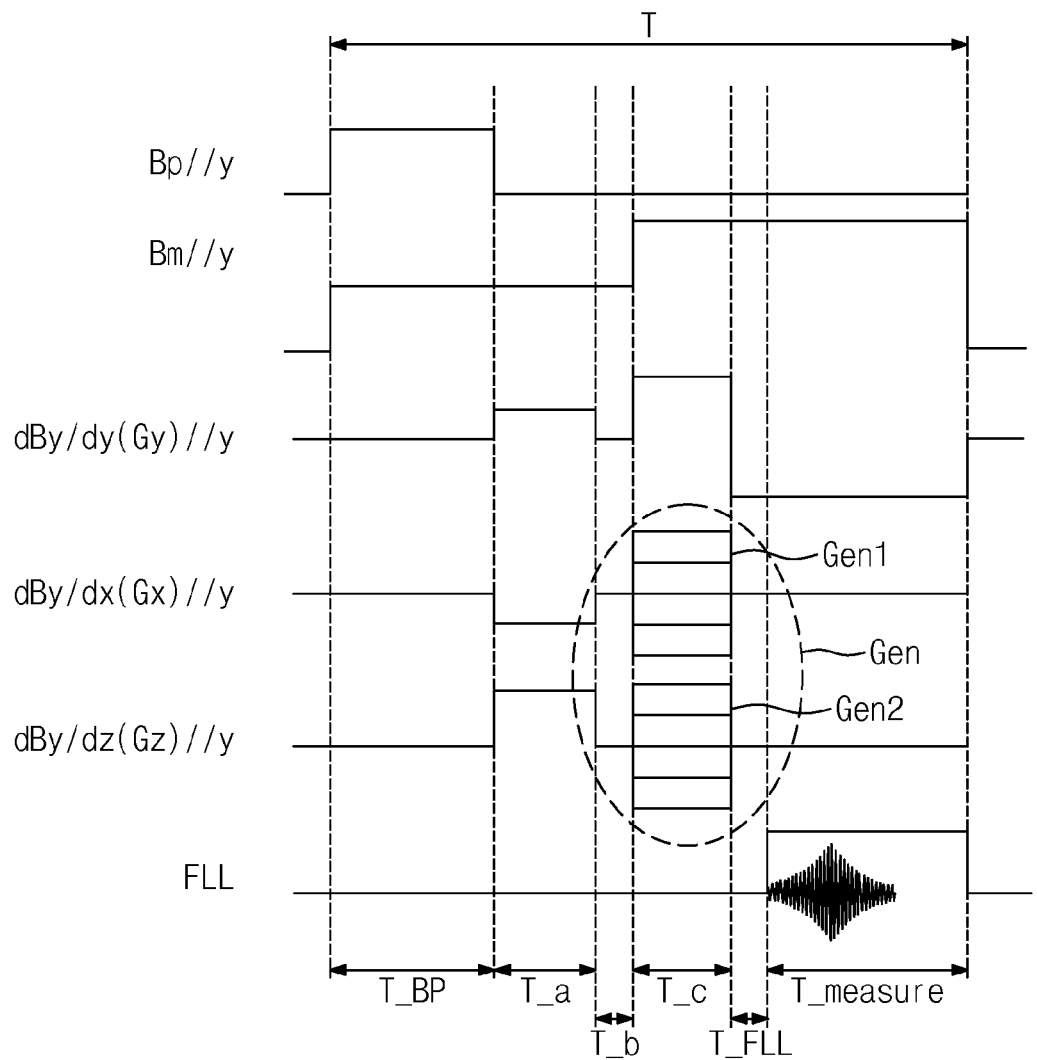

Referring to FIGS. 12, 13, and 10A, the nuclear magnetic resonance measuring method includes applying a first measurement bias magnetic field with a Larmor frequency corresponding to an oscillation frequency of a periodical coherent biomagnetic field generated in association with the electrophysiological activity of human body organs (S130), applying a second measurement bias magnetic field having the same direction as the first measurement bias magnetic field and having a different magnitude than the first measurement bias magnetic field (S140); and separating a frequency of a magnetic resonance signal generated in the human body from the oscillation frequency of the biomagnetic field by applying the second measurement bias magnetic field and measuring the magnetic resonance signal using magnetic field measuring means (S160). A coherent biomagnetic field may have a component on a plane perpendicular to the first measurement bias magnetic field. Thus, the coherent biomagnetic field may perform functions of a B1-RF magnetic field in conventional high magnetic field MRI.

A pre-polarization magnetic field may be applied to pre-polarize the human body using pre-polarizing means. Next, the pre-polarization magnetic field may be deactivated. Thus, the human body or measurement target may be pre-polarized. Preferably, a direction of the pre-polarization magnetic field may match that of the first measurement bias magnetic field.

When an oscillation frequency of the coherent biomagnetic field is not known, the magnitude of the first measurement bias magnetic field may be scanned such that a proton magnetic resonance frequency of the first measurement bias magnetic field matches the oscillation frequency of the coherent biomagnetic field. In this case, the second measurement bias magnetic field may be constant and fixed. Thus, the magnitude of the first measurement bias magnetic field may be selected by monitoring a frequency component corresponding to the second measurement bias magnetic field.

The magnetic field measuring means may be a superconducting quantum interference device or an optically pumped atomic magnetometer.

A gradient magnetic field may be provided to the human body (S150). The gradient magnetic field may include a resonance region selection gradient magnetic field (S152), a gradient echo magnetic field (S154), and an encoding gradient magnetic field (S156).

The gradient echo magnetic field (S154) may be applied to generate a gradient echo signal. The resonance region selection gradient magnetic field (S152) may be applied to select a specific resonant region. The encoding gradient magnetic field (S156) may be used in two-dimensional image or one-dimensional imaging.

A resonance region selection gradient magnetic field may include a first resonance region selection gradient magnetic field Gr1, a second resonance region selection gradient magnetic field Gr2, and a third resonance region selection gradient magnetic field Gr3. The first resonance region selection gradient magnetic field Gr1, the second resonance region selection gradient magnetic field Gr2, and the third resonance region selection gradient magnetic field Gr3 may provide gradient magnetic fields with respect to different directions. The resonance region selection gradient magnetic field may be applied before the second measurement bias magnetic field Bm2 is applied. Thus, a specific region may resonate with the coherent biomagnetic field due to the resonance region selection magnetic field.

The magnitude of the resonance region selection gradient magnetic field may be scanned such that the sum of the magnitude of the resonance region selection gradient magnetic field and the magnitude of the first measurement magnetic field corresponds to the oscillation frequency of the coherent biomagnetic field. Thus, a selected region may be changed.

The gradient echo magnetic field may be applied after the second measurement bias magnetic field Bm2. The gradient echo magnetic field may include a first gradient echo magnetic field Ge1 and a second gradient echo magnetic field Ge2 that are successively generated. The first gradient echo magnetic field Ge1 and the second gradient echo magnetic field Ge2 may be opposite in direction.

The encoding gradient magnetic field may be applied after the second measurement bias magnetic field Bm2 is applied. The encoding gradient magnetic field may include a first encoding gradient magnetic field and a second encoding gradient magnetic field. The encoding gradient magnetic field may perform at least one of frequency encoding and phase encoding.

A gradient echo signal may be measured after removal of the first gradient echo magnetic field Ge1. The gradient echo signal may be Fourier-transformed and processed. The gradient echo signal may be obtained while an FLL operates.

FIG. 14 is a flowchart summarizing a nuclear magnetic resonance measuring method according to another embodiment of the present invention.

Referring to FIG. 14, the nuclear magnetic resonance measuring method includes selecting a resonant region such that a coherent biomagnetic field having an oscillation frequency generated in association with electrophysiological activity of human organs magnetically resonates with protons precessing by a first measurement bias magnetic field (S210) and spatially imaging a resonant region selected under a second measurement bias magnetic field having the same direction as the first measurement bias magnetic field and having different magnitude than the first measurement bias magnetic field (S220).

The operation of selecting the resonant region (S210) may include applying a pre-polarization magnetic field to pre-polarize a human body (S212), applying a first measurement bias magnetic field having the same direction as the pre-polarization magnetic field and being spatially uniform to allow protons to precess (S214), applying a resonance region selection gradient magnetic field having the same direction as the first measurement bias magnetic field and spatially having a gradient (S216), and exciting the protons precessed by the first measurement bias magnetic field or the resonance region selection gradient magnetic field magnetically to resonate with the coherent biomagnetic field in a predetermined space or region (S218), resonance region selection The operation of spatially imaging a resonant region (S220) may include applying a second measurement bias magnetic field having the same direction as the first measurement bias magnetic field and having different magnitude than the first measurement bias magnetic field to the human body (S222), successively applying a first gradient echo magnetic field and a second gradient echo magnetic field to generate a gradient echo signal (S224), applying an encoding gradient magnetic field while applying the first gradient echo magnetic field (S226), and measuring the gradient echo signal while applying the second gradient echo magnetic field (S228). The encoding gradient magnetic field may include at least one of a phase encoding gradient magnetic field and a frequency encoding gradient magnetic field.

As described so far, a nuclear magnetic resonance measuring method according to an embodiment of the present invention is non-contact and non-invasive and may provide superior time and spatial resolution. Thus, minute change of activity current generated in the brain or heart may be accurately measured. As a result, the nuclear magnetic resonance measuring method may be used in function study and functional disease diagnosis of brain, heart or the like.

Although the present invention has been described in connection with the embodiment of the present invention illustrated in the accompanying drawings, it is not limited thereto. It will be apparent to those skilled in the art that various substitutions, modifications and changes may be made without departing from the scope and spirit of the present invention.

What is claimed is:
1. An ultra-low-field nuclear magnetic resonance measuring method comprising:
applying a first measurement bias magnetic field with a Larmor frequency corresponding to an oscillation frequency of a periodical coherent biomagnetic field generated in association with electrophysiological activity of human body organs;
applying a second measurement bias magnetic field, which has a same direction as the first measurement bias magnetic field and a higher magnitude than the first measurement bias magnetic field; and
separating a frequency of a magnetic resonance signal generated in a human body from the oscillation frequency by applying the second measurement bias magnetic field and measuring the magnetic resonance signal using a magnetic field measuring device, wherein the periodical coherent biomagnetic field is sustained after the second measurement bias magnetic field is applied, wherein the first measurement bias magnetic field is non-adiabatically changed into the second measurement bias magnetic field, and wherein the magnetic field measuring device comprises a superconducting quantum interference device (SQUID) or an optically pumped atomic magnetometer.

2. The ultra-low-field nuclear magnetic resonance measuring method of claim 1, wherein the periodical coherent biomagnetic field has a component on a plane perpendicular to the first measurement bias magnetic field.

3. The ultra-low-field nuclear magnetic resonance measuring method of claim 1, comprising applying a pre-polarization magnetic field to pre-polarize the human body using a pre-polarizing coil; and deactivating the pre-polarization magnetic field before measuring the magnetic resonance signal.

4. The ultra-low-field nuclear magnetic resonance measuring method of claim 3, wherein a direction of the pre-polarization magnetic field matches that of the first measurement bias magnetic field.

5. The ultra-low-field nuclear magnetic resonance measuring method of claim 1, comprising scanning the magnitude of the first measurement bias magnetic field such that a proton magnetic resonance frequency of the first measurement bias magnetic field matches the oscillation frequency.

6. The ultra-low-field nuclear magnetic resonance measuring method of claim 1, comprising providing a gradient magnetic field to the human body.

7. The ultra-low-field nuclear magnetic resonance measuring method of claim 6, wherein the gradient magnetic field includes at least one of a resonance region selection gradient magnetic field, a gradient echo magnetic field, and an encoding gradient magnetic field.

8. The ultra-low-field nuclear magnetic resonance measuring method of claim 7, wherein the gradient magnetic field comprises the resonance region selection gradient magnetic field, which includes at least one of a first resonance region selection gradient magnetic field, a second resonance region selection gradient magnetic field, and a third resonance region selection gradient magnetic field, wherein the first resonance region selection gradient magnetic field, the second resonance region selection gradient magnetic field, and the third resonance region selection gradient magnetic field provide gradient magnetic fields with respect to different directions, and wherein the resonance region selection gradient magnetic field is applied before the second measurement bias magnetic field is applied.

9. The ultra-low-field nuclear magnetic resonance measuring method of claim 7, wherein the gradient magnetic field comprises the resonance region selection gradient magnetic field and the resonance region selection gradient magnetic field is scanned in a condition such that a sum of the resonance region selection gradient magnetic field and the first measurement bias magnetic field corresponds to the oscillation frequency.

10. The ultra-low-field nuclear magnetic resonance measuring method of claim 7, wherein the gradient magnetic field comprises the gradient echo magnetic field, which is applied after the second measurement bias magnetic field is applied, wherein the gradient echo magnetic field includes a first gradient echo magnetic field and a second gradient echo magnetic field that are successively generated, and wherein the first gradient echo magnetic field and the second gradient echo magnetic field are opposite in direction.

11. The ultra-low-field nuclear magnetic resonance measuring method of claim 7, wherein the gradient magnetic field comprises the encoding gradient magnetic field, which is applied after the second measurement bias magnetic field is applied, wherein the encoding gradient magnetic field includes at least one of a first encoding gradient magnetic field and a second encoding gradient magnetic field, and wherein the encoding gradient magnetic field performs at least one of frequency encoding and phase encoding.

12. A nuclear magnetic resonance measuring method comprising:

selecting a resonant region such that a coherent biomagnetic field, which has an oscillation frequency generated in association with electrophysiological activity of human organs, magnetically resonates with protons processing by a first measurement bias magnetic field; and spatially imaging a resonant region selected under a second measurement bias magnetic field, which has a same direction as the first measurement bias magnetic field and a different magnitude than the first measurement bias magnetic field, with a magnetic field measuring device, wherein the coherent biomagnetic field is sustained after the second measurement bias magnetic field is applied, wherein the first measurement bias magnetic field is non-adiabatically changed into the second measurement bias magnetic field, wherein the magnetic field measuring device comprises a superconducting quantum interference device (SQUID) or an optically pumped atomic magnetometer, and wherein the second measurement bias magnetic field has a higher magnitude than the first measurement bias magnetic field.

13. The nuclear magnetic resonance measuring method of claim 12, wherein selecting the resonant region comprises at least one of:

applying a pre-polarization magnetic field to pre-polarize a human body;

applying the first measurement bias magnetic field, which has a same direction as the pre-polarization magnetic field and is spatially uniform to allow one or more protons to precess;

applying a resonance region selection gradient magnetic field having a same direction as the first measurement bias magnetic field and spatially having a gradient; and exciting the protons precessed by the first measurement bias magnetic field or the resonance region selection gradient magnetic field magnetically to resonate with the coherent biomagnetic field in a predetermined space or region.

14. The nuclear magnetic resonance measuring method of claim 12, wherein spatially imaging the resonant region comprises at least one of:

applying the second measurement bias magnetic field, which has a same direction as the first measurement bias magnetic field and a different magnitude than the first measurement bias magnetic field, to the human body;

successively applying a first gradient echo magnetic field and a second gradient echo magnetic field to generate a gradient echo signal;

applying an encoding gradient magnetic field while applying the first gradient echo magnetic field; and measuring the gradient echo signal while applying the second gradient echo magnetic field.

15. The nuclear magnetic resonance measuring method of claim 14 wherein spatially imaging the resonant region comprises applying the encoding gradient magnetic field while applying the first gradient echo magnetic field, and wherein the encoding gradient magnetic field includes at least one of a phase encoding gradient magnetic field and a frequency encoding gradient magnetic field.

16. An ultra-low-field nuclear magnetic resonance measuring device comprising:
   a magnetically shielding room;
   a magnetic field measuring device disposed adjacent to a measurement target disposed inside the magnetically shielding moans room; and
   a measurement bias magnetic field generating coil for applying a first measurement bias magnetic field corresponding to a proton magnetic resonance frequency matching an oscillation frequency of a coherent biomagnetic field generated in association with electrophysiological activity of human organs and successively changing a magnitude of the first measurement bias magnetic field to apply a second measurement bias magnetic field,
   wherein the magnetic field measuring device measures a magnetic resonance signal generated from the measurement target,
   wherein the coherent biomagnetic field is sustained after the second measurement bias magnetic field is applied,
   wherein the first measurement bias magnetic field is non-adiabatically changed into the second measurement bias magnetic field,
   wherein the second measurement bias magnetic field has a higher magnitude than the first measurement bias magnetic field, and
   wherein the magnetic field measuring device comprises a superconducting quantum interference device (SQUID) or an optically pumped atomic magnetometer.

17. The ultra-low-field nuclear magnetic resonance measuring device of claim 16, comprising a pre-polarizing coil for pre-polarizing the measurement target.

18. The ultra-low-field nuclear magnetic resonance measuring device of claim 16, comprising a gradient magnetic field generating coil for providing a gradient magnetic field to the measurement target.

19. The ultra-low-field nuclear magnetic resonance measuring device of claim 18, wherein the gradient magnetic field generating coil comprises at least one of:
   a resonance region selection gradient magnetic field generating coil for selecting a resonant region;
   a gradient echo magnetic field generating coil for generating a gradient echo signal; and
   an encoding gradient magnetic field generating coil for generating an encoding gradient magnetic field.

20. The ultra-low-field nuclear magnetic resonance measuring device of claim 16, wherein the first measurement bias magnetic field is configured to be scanned.

21. A brain functional connectivity measuring method for measuring and spatially imaging a magnetic resonance signal generated from protons resonating by a coherent biomagnetic field of a specific frequency in a brain by using an ultra-low-field nuclear magnetic resonance device to detect brain function connectivity, the method comprising:
   applying a first measurement bias magnetic field with a Larmor frequency corresponding to an oscillation frequency of a brainwave magnetic field generated in association with the brain function connectivity;
   applying a second measurement bias magnetic field, which has a same direction as the first measurement bias magnetic field and a different magnitude than the first measurement bias magnetic field; and
   separating a frequency of the magnetic resonance signal generated in a brain from the oscillation frequency of the brainwave magnetic field by applying the second measurement bias magnetic field and measuring the magnetic resonance signal using a magnetic field measuring device,
   wherein the coherent biomagnetic field is sustained after the second measurement bias magnetic field is applied,
   wherein the first measurement bias magnetic field is non-adiabatically changed into the second measurement bias magnetic field,
   wherein the second measurement bias magnetic field has a higher magnitude than the first measurement bias magnetic field, and
   wherein the magnetic field measuring device comprises a superconducting quantum interference device (SQUID) or an optically pumped atomic magnetometer.

* * * * *